United States Patent [19]

Yamanishi et al.

[11] Patent Number: 4,778,753
[45] Date of Patent: * Oct. 18, 1988

[54] METHOD OF QUANTITATIVELY MEASURING AN OXIDATIVE SUBSTANCE USING TRIPHENYL METHANE TYPE LEUCO-PIGMENT AS A COLORING SUBSTANCE

[75] Inventors: Kazuhiko Yamanishi, Tokyo; Toshiro Hanada, Saitama, both of Japan

[73] Assignee: Wako Pure Chemical Industries Ltd., Osaka, Japan

[*] Notice: The portion of the term of this patent subsequent to Jun. 16, 2004 has been disclaimed.

[21] Appl. No.: 649,479

[22] Filed: Sep. 11, 1984

[30] Foreign Application Priority Data

Mar. 15, 1984 [JP] Japan ................................ 59-49950
Apr. 2, 1984 [JP] Japan ................................ 59-65629
Apr. 10, 1984 [JP] Japan ................................ 59-71548

[51] Int. Cl.$^4$ .................. C12Q 1/26; C12Q 1/28; C12Q 1/54; C12Q 1/60
[52] U.S. Cl. ........................... 435/10; 435/11; 435/12; 435/28; 435/14; 435/904; 436/66; 436/71; 436/135; 436/164
[58] Field of Search .................. 544/347; 435/12, 10, 435/28, 11, 14; 436/825, 826, 71, 66, 135, 164, 904; 424/7.1

[56] References Cited

U.S. PATENT DOCUMENTS

| | | | |
|---|---|---|---|
| 2,850,359 | 9/1958 | Worthington et al. | 435/10 |
| 4,317,878 | 3/1982 | Nakanishi et al. | 435/10 |
| 4,330,476 | 5/1982 | Hermann | 546/152 |
| 4,433,060 | 2/1984 | Frenzel | 436/536 |
| 4,554,249 | 11/1985 | Kosaka | 436/825 |
| 4,673,635 | 6/1987 | Yamanishi et al. | 435/10 |

FOREIGN PATENT DOCUMENTS

3124590 1/1983 Fed. Rep. of Germany ........ 435/28

Primary Examiner—Robert J. Warden
Assistant Examiner—Stephen C. Wieder
Attorney, Agent, or Firm—Cushman, Darby & Cushman

[57] ABSTRACT

Disclosed herein is a method of quantitatively measuring an oxidative substance with avoiding influences of a coloring-interfering substance in the quantitative measurement of the oxidative substance by using a triphenyl methane type leuco coloring matter as a coloring reagent. Disclosed herein is also such an oxidative quantitative measurement in which the coloring sensitivity can be further adjusted. In order to avoid the influences of the coloring-interfering substance, there is employed at least one kind of (i) uricase, (ii) an anionic surface active agent and (iii) a metal chelate compound. As the triphenyl methane type leuco coloring matter, use may be made of a compound of the general formula (I):

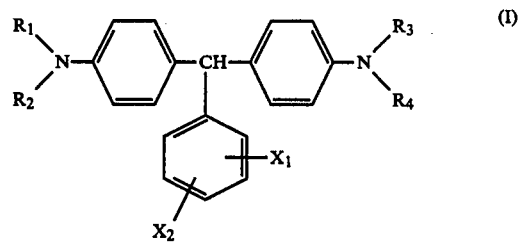

wherein $R_1$, $R_2$, $R_3$ and $R_4$, which may be the same as or different from one another, represent a hydrogen atom or a lower alkyl group, and $X_1$ and $X_2$, which may be the same as or different from each other, represent a hydrogen atom, $-SO_3M_1$, $-COOM_2$, $-O(CH_2)_mSO_3M_3$, $-O(CH_2)_nCOOM_4$ or $-N(R_5)(R_6)$ in which $M_1$, $M_2$, $M_3$ and $M_4$ represent a hydrogen atom, an alkali metal ion or $NH_4^+$, $R_5$ and $R_6$ independently represent a hydrogen atom or a lower alkyl group, and m and n represent an integer of 2-4. Azide compound is further added or the compound represented by the general formula (I) is included with cyclodextrin or modified dextrine to adjust coloring sensitivity.

29 Claims, 15 Drawing Sheets

METHOD OF QUANTITATIVELY MEASURING AN OXIDATIVE SUBSTANCE USING TRIPHENYL METHANE TYPE LEUCO-PIGMENT AS A COLORING SUBSTANCE

BACKGROUND OF THE INVENTION (1) Field of the Invention:

The present invention relates to a method of quantitatively measuring an oxidative substance while avoiding the influences of a coloring-interfering substance in the quantitative measurement of a component in a body fluid by using a triphenyl methane type leuco-pigment as a coloring reagent. The invention also relates to a method of quantitatively measuring an oxidative substance with coloring sensitivity thereof being adjustable in such a quantitative measurement of the body fluid component.

(2) Description of the Prior Art:

Triphenyl methane type leuco-pigment is superior to the conventional oxidizable coloring reagents in that when oxidatively colored, the pigment has a coloring wavelength of not less than 600 nm on the long wavelength side, and a large molecular absorption coefficient of not less than 50,000. In addition, the color does not fade over time after color development. Thus, they have been experimentally applied to the quantitative measurement of a very small amount of an oxidative substance such as hydrogen peroxide or a quantitative measurement of peroxidase-like substance, and the like. For instance, it is reported in Analytical Chemistry Vol. 42, p. 410-411 (1970) that $H_{2p}O_2$ can be quantitatively measured by using a combined reagent of leucocrystal violet (LCV) and peroxidase (POD). In Clinical Chemistry Vol. 21, p. 362-369 (1975), there are reported experimental results in the quantitative measurement of heme compounds such as hemoglobin and the like using leucomalachite green (LMG) and $H_2O_2$. However, the quantitative measurement of $H_2O_2$ in the former case is merely an ordinary $H_2O_2$ quantitative measurement. It does not refer to the quantitative measurement of $H_2O_2$ generated by an enzyme reaction in the quantitative measurement of the component in the body fluid where linearity lineality of a calibration curve is poor due to the influences of protein in samples. Meanwhile, Japanese Patent Application Laid Open No. 26,199/1981 discloses a method of quantitatively measuring a component present in a very small amount in serum, urine or the like using bis(p-diethylaminophenyl)-2-sulfophenyl methane (hereinafter abbreviated as BSPM), which belongs to the triphenyl methane type leuco coloring matters. According to the trace experiment of the present inventors, quantitative determinations, described in the specification of this publication, could not be obtained with serum. That is, the triphenyl methane type leuco-pigment has not seen practical use in the field of clinical chemical analysis.

On the other hand, a triphenyl methane type leuco coloring matter of a high sensitivity has been developed and its practical application is expected. Compared with the conventional oxidizable coloring reagent, this coloring reagent has the advantages that the coloring wavelength is on the long wavelength side, not less than 600 nm, the molecular absorption coefficient is not less than 70,000, and almost no color fading takes place with a lapse of time after color development. However, due to its high sensitivity, there may be difficulties in practice. That is, its use is limited to a narrow measuring range of the quantitative measurement of an extremely small amount of hydrogen peroxide owing to its high sensitivity. For instance, in the measurement of hydrogen peroxide at such a concentration as to be satisfactorily measured at a measuring sensitivity equivalent to that of 4-aminoantipyrine-phenol type, there are practical problems. That is, a sample must be taken in an extremely small amount (for example, not more than 10 $\mu$l), and therefore pipeting error becomes larger, resulting in variation of the measured values. In addition, a sample must first be diluted so as to lessen the errors in sampling. Accordingly, if there were available a method which would allow the adjustment of the sensitivity of the triphenyl methane derivative (which has the advantages, for instance, of a coloring wavelength on the long wavelength side and suffers almost no color fading with a lapse of time after color development over a wide range of around 5,000 on the lower side up to 100,000 or more on the high sensitivity upper side, its application would be greatly widened and advantages, unexpected in the conventional coloring reagents, would be anticipated.

SUMMARY OF THE INVENTION

It is therefore an object of the present invention to provide a method of quantitatively measuring an oxidative substance while avoiding the influences of a coloring-interfering substance.

It is another object of the present invention to provide a method of quantitatively measuring an oxidative substance, which method enables the adjustment of a coloring sensitivity.

It is a still another object of the invention to provide a method of quantitatively measuring an oxidative substance by using a novel coloring reagent which has excellent solubility aqueous solutions in the neutral range, and is stable in coloring, and exhibits a color having an absorption on a long wavelength side which makes the coloring not likely to be influenced by components in serum.

According to the invention, there is a provision of a method of quantitatively measuring the oxidative substance by using as a coloring reagent a triphenyl methane type leuco coloring matter of the following formula and a member selected from the group consisting of (i) uricase and (ii) anionic surface active agent and a metal chelate compound, whereby the influences of the coloring-interfering substance are avoided:

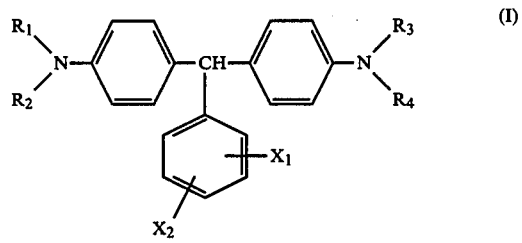

wherein $R_1$, $R_2$, $R_3$ and $R_4$, which may be the same as or different from one another, represent a hydrogen atom or a lower alkyl group, and $X_1$ and $X_2$, which may be the same as or different from each other, represent a hydrogen atom, $-SO_3M_1$, $-COOM_2$, $-O(CH_2)_mSO_3M_3$, $-O(CH_2)_nCOOM_4$ or $-N(R_5)(R_6)$ in which $M_1$, $M_2$, $M_3$ and $M_4$ represent a hydrogen atom, an alkali metal ion or $NH_4^+$ $R_5$ and $R_6$ independently represent a hydrogen atom or a lower alkyl group, and m and n represent an integer of 2-4.

According to the another aspect of the invention, in the method of quantitatively measuring the oxidative substance while avoiding the influences of the coloring-interfering substance, an azide compound is further used or the compound represented by the general formula (I) is included with cyclodextrin or modified cyclodextrin, whereby the coloring sensitivity is adjusted.

Other objects, features and advantages of the invention will be well appreciated upon reading of the following description of the invention when taken in conjunction with the accompanying drawings, with the understanding that some modifications, variations and changes could be easily done by the skilled in one art to which the invention pertains, without departing from the spirit of the invention and the scope of the claims appended hereto.

DETAILED DESCRIPTION OF THE INVENTION

Figure 1:
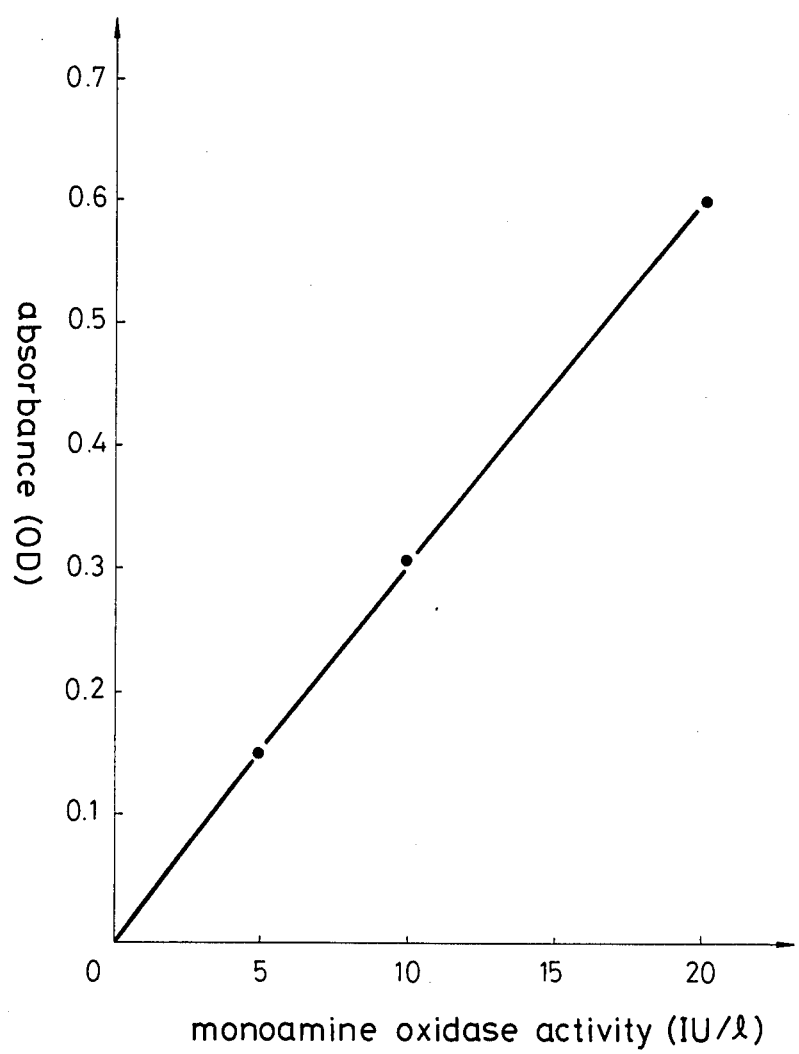
FIG. 1 shows a calibration curve obtained in Example 1 in which absorbances (OD) are plotted on the ordinate with respect to the respective monoamine oxidase activities (IU/l) one the abscissa, and plotted points are connected.

Having studied the coloring-interfering substances which influence the oxidation coloring of the triphenyl methane type leuco-pigment in the quantitative measurement of components in body fluids, the present inventors have found that protein and uric acid are the cause therefor particularly, uric acid interfers the coloring to a large extent. As a result of further studies on a method of avoiding the influences of these interfering substances, the inventors have found that the influences of protein are avoided through the addition of specific surface active agents or specific metal chelates, and those of uric acid are avoided through the addition of uricase, to attain the intended objects of the invention, and accordingly they have accomplished the invention.

That is, the present invention relates to a method of quantitatively measuring the amount of $H_2O_2$ while avoiding the influences of a coloring-interfering substance by using (i) uricase and/or (ii) anionic surface active agent or a metal chelate compound singly or a mixture of two or more thereof in the quantitative measurement of a component in a body fluid by using as a coloring reagent a triphenyl methane type leuco-pigment represented by the following general formula (I):

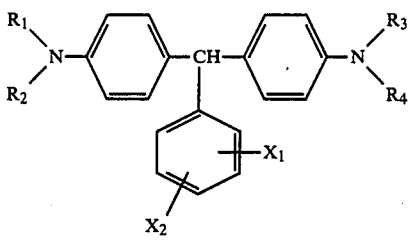

wherein $R_1$, $R_2$, $R_3$ and $R_4$, which may be the same as or different from one another, represent a hydrogen atom or a lower alkyl group, and $X_1$ and $X_2$, which may be the same as or different from each other, represent a hydrogen atom, $-SO_3M_1$, $-COOM_2$, $-O(CH_2)_mSO_3M_3$, $-O(CH_2)_nCOOM_4$ or $-N(R_5)(R_6)$ in which $M_1$, $M_2$, $M_3$ and $M_4$ represent a hydrogen atom, an alkali metal ion or $NH_4^+$, $R_5$ and $R_6$ independently represent a hydrogen atom or a lower alkyl group, and m and n represent an integer of 2-4.

Thus, the method of quantitatively measuring an oxidative substance by using the leuco coloring matter according to the present invention is applicable without any trouble to the measurement of chemical components in the body fluids such as serum or urine, containing uric acid and protein, by the enzyme method ($H_2O_2$ generation system).

The method of quantitatively measuring $H_2O_2$, while with avoiding the influences of the coloring-interfering substance according to the present invention, can be used in the quantitative measurement of the components in the body fluid by using the triphenyl methane type leuco-pigment as the coloring reagent based on the enzyme method ($H_2O_2$-POD system), for instance, the quantitative measurement of a substrate such as glucose, cholesterol, triglyceride, phospholipid, choline, creatine, creatinine, bile acid and the like in the body fluids, and in the enzyme activity measurement of monoamine oxidase and the like, and in the quantitative measurement of a peroxidase-like substance such as hemoglogin or the like in the body fluid by using $H_2O_2$.

In practicing the method of the invention with respect to the serum, the concentration of more than 0.01 mM of the triphenyl methane type oxidizable coloring reagent in the invention is adoptable, and ordinarily 0.02-0.3 mM of the concentration is preferably adopted.

As the surface active agents effectively used in the present invention for avoiding the interference of protein, generally anionic surface active agents, particularly the ones represented by the following formulae (II) and (III), are effective.

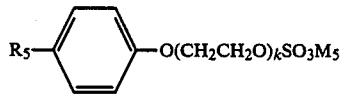

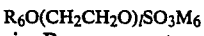

wherein $R_5$ represents an alkyl group of 8-9 carbon atoms, $R_6$ represents an alkyl group of 8-18 carbon atoms, $M_5$ and $M_6$ each represent an alkali metal ion, an ammonium ion, or a quaternary ammonium ion, and k and l each represent an integer of 1-6. As specific examples corresponding to the compound of the general formula (II), mention may be made of Emal NC(polyoxyethylene alkylphenyl ether sodium sulfate; trademark of Kao Soap Co., Ltd.), Nicol 560 SF (polyoxyethylene nonylphenyl ether ammonium sulfate; trademark of Nippon Emulsifier Co., Ltd.), Nicol SNP-4T (polyoxyethylene nonylphenyl ether triethanolamine sulfate; trademark of Nippon Emulsifier Co., Ltd.). As specific examples corresponding to the compound of the general formula (III), mention may be made of Emal 20 C (polyoxyethylene alkyl ether sodium sulfate; trademark of Kao Soap Co., Ltd.), Sannol 605 D (polyoxyethylene alkyl ether sodium sulfate; trademark of Lion Co., Ltd.) Nicol NES-303 (polyoxyethylene alkyl ether triethanolamine sulfate; trademark of Nikko Chemicals Co., Ltd.). As a matter of course, the invention is not limited to those specifically mentioned above. These surface active agents are each ordinarily used at the actual concentration of 0.01-10% in the coloring reagent solution.

As the metal chelate compounds effective for removing the interference of protein, generally a metal-EDTA (ethylenediamine tetraacetic acid) is effectively used. As specific examples of the chelate, mention may be made of, for instance, Fe(III)-EDTA, Mn(II)-EDTA, Ni(II)-EDTA and the like, but they are not restrictive. All the ordinary metal-EDTA chelates commercially available may be used. Effect can be observed at the addition amount of not less than 0.005%, and ordinarily 0.01-0.5% is preferably adopted.

Meanwhile, uricase used for avoiding the interference of uric acid, is an oxidative enzyme of uric acid, and acts upon the uric acid to be converted into allantoin, hydrogen peroxide and carbon dioxide. According to the present invention, uric acid can be decomposed without being accompanied by the formation of $H_2O_2$ by acting uricase upon the uric acid in the presence of the triphenyl methane derivative and peroxidase. Thus, the triphenyl methane type leuco-pigment is not colored at all through oxidization by hydrogen peroxide produced through the decomposition of uric acid, and uric acid as the interfering substance can be extremely easily and effectively removed. The addition of an amount of uricase may be generally not less than 50 U/l, and a range of 100-500 U/l is preferably adopted. That is, in order to remove the interference of uric acid, when a reagent solution containing 0.01-0.3 m mol/l of the triphenyl methane type leuco-pigment is used, 50-500 U/l of uricase, 100-10,000 U/l of peroxidase, and appropriate amount of a surface active agent if necessary in a buffer solution of pH 6-8 is added to a sample containing uric acid. The uric acid is instantly decomposed. At that time, no hydrogen peroxide is generated and therefore, the triphenyl methane type leucopigment is not colored at all. It is presumed that the uric acid is decomposed by the conversion into alloxan, or a decomposition product thereof, and urea. There has been no literature describing the decomposition of uric acid by uricase unaccompanied by the generation of $H_2O_2$. The present inventors have found that while such a phenomenon is not recognized with respect to other oxidizable coloring reagent, it is an effect peculiar to the triphenyl leuco-pigment. This phenomenon is beyond anticipation in that an action utterly different from the ordinary enzyme action of the uricase upon uric acid is induced from uricase.

Since both protein and uric acid are ordinarily present in serum, when the component in the body fluid is measured according to the enzyme method ($H_2O_2$—POD system) or hemoglobin in the serum is measured according to the $H_2O_2$ system by using the triphenyl methane type leuco-pigment as a coloring reagent, the interferences of both the protein and the uric acid can be avoided by the combined use of the anionic surface active agent or metal chelate compound and uricase according to the present invention, so that more precisely measured value can be easily obtained.

With respect to the triphenyl methane type leuco-pigment used as the coloring reagent according to the method of the invention in which the influences of the coloring-interfering substances are avoided, it is possible to use. All the triphenyl methane type leuco-pigment represented by the above general formula (I) which may be used as the coloring reagent. Mention may be specifically made of, for example, leucocrystal violet, leucomalachite green, BSPM, bis(4-N,N-diethylaminophenyl)-4-sodium sulfopropoxyphenyl methane (hereinafter abbreviated as BSproPM) and bis(4-N,N-diethylaminophenyl)-3,4-disodium sulfopropoxyphenyl methane (hereinafter abbreviated as BSdiproPM) and the like.

The triphenyl methane derivatives of the following general formula (IV) encompassed by the above general formula (I) are novel compounds.

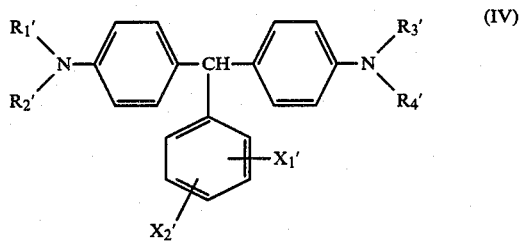

wherein $R_1'$, $R_2'$, $R_3'$ and $R_4'$, which may be the same as or different represent $-O(CH_2)_n SO_3M'$ in which $M'$ is a hydrogen atom, an alkali metal ion or $NH_4^+$, and $n'$ is an integer of 2–4, or either of $X_1'$ and $X_2'$ represents $-O(CH_2)_n SO_3M'$ in which $M'$ and $n'$ are the same meanings as given above and the other represents a hydrogen atom.

These compounds may be generally produced by the following process. That is, for instance, in the case of bis(4-N,N-diethylaminophenyl)-3,4-disodium sulfopropoxyphenyl methane, protocatechualdehyde and propane sulfone are reacted with each other, under heating, in an organic solvent such as methyl cellosolve, ethyl cellosolve or the like in the presence of an alkali such as caustic soda, sodium alcoholate or the like, and after the completion of the reaction, ordinary post-treatments such as cooling, crystal precipitation, solvent pouring, filtration, washing and so on are carried out, and if necessary, purification by a column chromatography or the like is carried out to obtain 3,4-disodiumsulfopropoxybenzaldehyde. Then, the resultant is reacted with N,N-diethylaniline in an organic solvent such as methyl cellosolve, ethyl cellosolve or the like under heating in the presence of a catalyst such as zinc chloride or the like, and post-treatments are done in the ordinary way and purification is carried out by a column chromatography or the like to obtain the intended product. Generally, the other compounds encompassed by the general formula (I) may be produced in the same or similar manner.

The leuco coloring matters represented by the general formula (IV) in the present invention are high in water solubility and extremely stable even in a solution that they undergo no change at room temperature for 24 hour storage. Further, since their coloring sensitivity is at least $\epsilon$ 80,000 and $\lambda_{max}$ is present on the long wavelength side, that is, 600–700 nm, they are not susceptible to interference by hemoglobin, bilirubin and the like.

Although the coloring reagents of the invention represented by the general formula (IV) are characterized by their high sensitivity, the high sensitivity in turn becomes an obstacle in the practical use. That is, due to the high sensitivity, a sample must be taken in an extremely small amount (for instance, 10 $\mu$l or less) when measuring the concentration of $H_2O_2$ if it is to be satisfactorily measured with a sensitivity equivalent to that of a 4-aminoantipyrinphenol type coloring reagent. Thus error in the measured value becomes sufficiently large to cause a variation thereof. It is necessary to initially dilute the sample in order to lessen the error incident to the sampling.

Such problems can be eliminated by a method according to the present invention by using an azide compound as a sensitivity adjustor or by including with the compound represented by the general formula (I) the cyclodextrin (hereinafter abbreviated as CD) or modified cyclodextrin (hereinafter abbreviated as modified CD) in the quantitative measurement of the oxidative substance using the triphenyl methane derivatives of the general formula (I) as a coloring reagent.

The azide compound, particularly, sodium azide, is generally used as antiseptics, and it is famous as an inhibitor against metal series enzyme such as a catalase, peroxidase, laccase and the like.

However, in the present invention, the fact that the effect, which has not been heretofore known with respect to the conventional azide compound (that is, the effect of adjusting the coloring sensitivity of the triphenyl methane derivatives), can be obtained by the combined use of the triphenyl methane derivatives and azide, enables the invention to be applied to a wide range of uses by utilizing the excellent characteristics of the triphenyl methane derivatives as the oxidizable coloring reagent (that is, the coloring wave is on the long wavelength side and almost no color is faded with lapse of time after color development) without the use of the triphenyl methane derivatives being restricted to the quantitative measurement of an extremely small amount of substances.

As the azide, use may be made of any one of alkali salt, alkaline earth metal salt, and other metal salt of hydrogen azide. Ordinarily, sodium azide is preferable. So long as the concentration of the azide in the coloring reagent solution is not less than 1.001%, the effect for the reduction in the coloring sensitivity is recognized, and ordinarily 0.01–0.5% is preferably adopted. For instance, in the case of BSdiproPM, the coloring sensitivity is lowered down to 16.5% at the largest by adding 0.2% of sodium azide to the coloring reagent solution, and its calibration curve becomes a straight line passing through the origin. Moreover, according to the present invention, it is possible to appropriately adjust the coloring sensitivity into a desired range by appropriately selecting the addition amount of the azide.

Meanwhile, it is known that when CD or modified CD is mixed with an organic compound in an aqueous solution, they ordinarily readily form an inclusion body, and therefore, they have excellent effects, for example, in stabilizing medicines, adjusting the solubility, pulverizing a liquid chemicals, masking stimulous and offensive odor and the like, adjusting the volatility, and they are accordingly used for the purposes thereof. In addition, it is considered that when CD or modified CD is added to the coloring reagent, the coloring sensitivity is ordinarily increased by the effect of the increasing the solubility, and therefore they are often used for this purpose, too.

However, according to the present invention, unexpectedly, the coloring sensitivity can be lowered by including the triphenyl methane derivatives with CD or modified CD, and consequently the derivative can be applied over a wide range of uses by virtue of its excellent characteristics, without being resitricted to the quantitative measurement of an extremely small amount of a substance.

In addition, since bis(p-diethylaminophenyl)2-sulfophenyl methane (BSPM) (Japanese Patent Application Laid-Open No. 26,199/1981) which is one of the triphenyl methane derivatives and a known compound as the coloring reagents is difficult to be completely dissolved even at the concentration f 0.01 mM in a buffer solution of pH 6-8 ordinarily adopted in the enzyme measurement method ($H_2O_2$ generation system) of an extremely small amount of a component in serum (ordinarily, it is once dissolved on the acidic range, and the pH is adjusted around the neutrality, but the usable concentration is 0.5 mM at the largest), it has been up to now difficult to put it into a practical use in this field. To the contrary, according to the present invention, the solubility is increased through inclusion by using Cd or modified CD, so that the triphenyl methane derivatives can be dissolved even at a concentration of 20 mM or more and its practical use is possible.

CD used in the present invention can be applicable in any of $\alpha$, $\beta$, $\gamma$, and $\delta$ forms. As the modified CD, mention may be made of, for instance, the compound of the following formula (V):

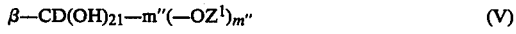

wherein CD represents cyclodextrin residue, $Z^1$ represents $-NO_2$, $-PO_3H$, $-SO_3H$ or a group of the formula: $-(CH_2)_{n''}Z^2$ in which $Z^2$ represents $-SO_3H$ or $-CO_2H$, and $n''$ is an integer of 1 to 4, and $m''$ represents an number of 1 to 5, and the compound of the general formula (VI):

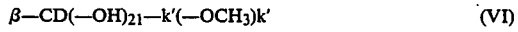

wherein k' represents a figure of higher than 0 but not higher than 21.

Typical examples of such $\beta$-cyclodextrin derivatives are enumerated by way of example as follows:

$\beta-CD(-OH)_{19}(-ONO_2)_2$
$\beta-CD(-OH)_{19.2}(-OPO_3H)_{1.8}$
$\beta-CD(-OH)_{19}(-OSO_3H)_2$
$\beta-CD(-OH)_{18.5}(-O-CH_2-CO_2H)_{2.5}$
$\beta-CD(-OH)_{19.3}(-O-CH_2CH_2CH_2-SO_3H)_{1.7}$
$\beta-CD(-OH)_{18.5}(-O-CH_2CH_2CH_2-SO_3H)_{2.5}$
$\beta-CD(-OH)_{18.0}(-O-CH_2CH_2CH_2-SO_3H)_{3.0}$
$\beta-CD(-OH)_{7}(-OCH_3)_{14}$
$\beta-CD(-OCH_3)_{21}$ However, the modified CD in the present invention is not restricted to these specific examples. These modified CD can be easily produced according to the ordinary producing processes described in the literatures. For instance, see Journal of Synthetic Organic Chemistry, Japan Vol. 35, No. 2, p 123 (41) to p 124 (42) (1977).

In order to include with CD or modified CD, the triphenyl methane derivatives may be added and dissolved into a solution in which CD or the modified CD is dissolved into water or a buffer solution. In this way, it is possible to easily dissolve BSPM, which is difficult to be dissolved in water or buffer solution, in a short time. The moles of CD or modified CD may be equal to or more than the moles of triphenyl methane derivatives. Ordinarily, 10-1,000 times as many moles are preferably used. By including the derivative with CD or modified CD, the coloring sensitivities are lowered to around 55.2% at the largest with respect to $\alpha$—CD inclusion, and around 37.4% at the largest with respect to $\beta$—CD inclusion in the case of BSPM; around 38.7% at the largest with respect to $\alpha$—CD inclusion and around 29.0% at the largest with respect to $\beta$—CD inclusion in the case of BSdiproPM; around 53.7% at the largest with respect to $\alpha$—CD inclusion and around 38.8% at the largest with respect to $\beta$—CD inclusion in the case of BSproPM.

According to the present invention, the use of azide, CD or modified CD makes utterly no influence upon the coloring speed.

The present invention will be explained in more detail with reference to Reference Examples and Examples. The Examples are given merely as illustration of the invention, but never interpreted as the limitation thereof. In the following, the thickness of a cell in the absorbance measurement was 10 mm in all cases.

REFERENCE EXAMPLE 1

Synthesis of BSdiproPM (1) Synthesis of 3,4-disodium sulfopropoxybenzaldehyde To 27.6 g (0.2 mol) of protocatechualdehyde dissolved in 200 ml of methanol was added 92.4 g (0.48 mol) of 28% sodium methylate, which was evaported to dryness. 400 ml of methyl cellosolve was added to the thus dried matter, which was dissolved under stirring. Then, 58.8 g (0.48 mol) of propanesulfone dissolved into 50 ml of methyl cellosolve was dropwise added to the solution at 95°-100° C., and after the completion of addition, the reaction was carried out at the same temperature under stirring for one hour. After cooling of the reaction liquid, acetone was added thereto to disperse crystals, and the crystals were filtered out, followed by drying, to obtain 88 g of crude crystals (yield 103.2%). The crude product was purified by a column chromatography (ODS reversed phase column chromatography, 20% methanol aqueous solution containing 5% of AcOH) to obtain 43.5 g of purified crystals. TLC: one spot, IR (Kbr): $\nu=1055$ ($-SO_3^{\ominus}$, $\phi-O-R$), 1190-1220 ($-SO_3^{\ominus}$, $\phi-O-R$), 1670 cm$^{-1}$ ($-CHO$).

(2) Synthesis of BSdiproPM

After 7.0 g (16.4 mmol) of the 3,4-disodium sulfopropoxybenzaldehyde obtained in (1), 7.3 g (49.2 mmol) of N,N-diethylaniline and 4.5 g of zinc chloride were suspended into 140 ml of methyl cellosolve, reaction was carried out at an internal temperature of 125° C. for 28 hours. During the reaction, water produced was distilled off. After the termination of the reaction, 300 ml of dimethyl sulfoxide was added to dissolve the reaction product, and insoluble matters were filtered off. 1,700 ml of ethyl acetate was added to the filtrate to precipitate crystals. The crystals were filtered out, and were dissolved into 15 ml of water. This solution was subjected to purification by a column chromatography (carrier Wakogel ® C-200), and the eluent was subjected to the distillation. The residue was dissolved in water, which was decolorized and filtered. After concentration of the filtrate, acetone was added to the concentrate to precipitate crystals, which was filtered out to obtain 2.68 g of the intended fine slightly blue crystals (yield: 23.2%).

|  | H | C | N |
|---|---|---|---|
| Calculated (%) | 6.27 | 56.08 | 3.96 |
| Found (%) | 6.46 | 56.06 | 4.14 |

UV(0.1M tris buffer solution, pH=7.5): $\lambda_{max}$ ($\epsilon$)=620 nm (166,300) IR(KBr): $\nu$=1020–1030 (—$SO_3^-$, $\phi$—O—R), 1180–1200 (—$SO_3^-$, $\phi$—O—R), 1380 (—N—$(C_2H_5)_2$), 2950 $cm^{-1}$ (—$C_2H_5$).

REFERENCE EXAMPLE 2

Synthesis of BSproPM

In accordance with Reference Example 1 (2), 2.5 g of 4-sodium sulfopropoxybenzaldehyde obtained from p-hydroxybenzaldehyde and propanesulfone similarly to Reference Example 1 (1) was reacted with 3.4 g of N,N-diethylaniline in 50 ml of methyl cellosolve in the presence of 2.4 g of zinc chloride, and post-treatment was carried out similarly to Reference Example 1 (2) to obtain 0.7 g of light blue crystals of 0.7 g of bis(4-N,N-diethylaminophenyl)-4-sodium sulfopropoxyphenyl methane (BSproPM) (yield: 13.6%).

|  | H | C | N |
|---|---|---|---|
| Calculated (%) | 7.19 | 65.91 | 5.12 |
| Found (%) | 7.33 | 65.94 | 5.28 |

UV (0.1 M tris buffer solution, pH=7.5): $\lambda_{max}$ ($\epsilon$)=620 nm (121,800)

EXAMPLE 1

Measurement of serum monoamine oxidase activity

Using 15 mM of allylamine as a substrate, uricase, BSdiproPM, Emal NC (Kao Atlas Co., Ltd.; trademark) and POD were dissolved into 20 mM of phosphate buffer solution (pH=7.0) to be in the respective concentrations of 200 U/l, 0.03 mM, 5% and 3,000 U/l to prepare a substrate color reagent.

8.9 mM aqueous solution of sodium diethyldithiocarbamate was prepared as a reaction terminator solution.

3 ml of the above substrate color reagent was added to 50 µl of a sampled serum, and incubated at 37° C. for 30 minutes. Then, 50 µl of the reaction terminator solution was mixed thereinto and absorbance at a wavelength of 620 nm was measured by using a reagent blank as control.

Using bovine monoamine oxidase manufactured by Sigma Co., Ltd., standard solutions of 5 IU/l, 10 IU/l, and 20 IU/l were prepared, and then absorbances were measured with respect to these standard solutions as in the case of the serum to obtain a calibration curve therefrom, which is shown in FIG. 1.

The activity of monoamine oxidase in the sample was determined from the calibration curve.

REFERENCE EXAMPLE 3

(Buffer solution)

30 mM of allylamine, 0.53 mM of phenol, and an appropriate amount of a surface active agent were added to 25 mM of Good's buffer solution (pH 6.75) to prepare a buffer solution.

(First reagent solution)

170 units of lipoprotein lipase, 425 units of ascorbate oxidase, 255 units of peroxidase and an appropriate of a stabilizer were added to 85 ml of the above prepared buffer solution to prepare a first reagent solution.

(Second reagent solution)

7.3 µmol of 10-N-methylcarbamoyl-3,7-dimethylamino-10H-phenothiazine (MCDP) and an appropriate amount of a stabilizer were added to 85 ml of the above prepared buffer solution to prepare a second reagent solution.

When in use, the first reagent solution and the second reagent solution were mixed with each other in the same volume to prepare a color reagent.

An aqueous solution of 8.9 mM of sodium diethyldithiocarbamate was prepared as a reaction terminator solution.

3.0 ml of the color reagent was taken, and preliminarily heated in a thermostatic oven of 37° C. for about 5 min., and 50 µl of serum was added thereto, followed by incubation at 37° C. for 30 min. Then, 50 µl of the reaction terminator solution was added to and mixed with the reaction solution, and absorbance (Es) was measured at a wavelength of 660 nm with reference to water as control.

By using 50 µl of monoamine oxidase standard solutions (prepared in Example 3) and 50 µl of purified water instead of the serum, absorbances Estd and $E_B$ were obtained as in the same procedure as above, and the activity of the monoamine oxidase was calculated by the following formula:

Monoamine oxidase activity $(IU/l) =$ $$\frac{Es - E_B}{Estd - E_B} \times \text{Standard enzyme activity}$$

Table 1 shows changes in the reagent blank in the storage of the color reagent (stored at 15° C.) in the cases of Example 1 and Reference Example 3.

TABLE 1

| Stored time (hour) | Example 1 | Reference Example 3 |
|---|---|---|
| 0 | 0.030 | 0.027 |
| 2 | 0.030 | 0.041 |
| 5 | 0.029 | 0.124 |
| 7 | 0.030 | 0.172 |
| 24 | 0.031 | could not be measured |

As shown in Table 1, in the case of Reference Example 3, since the reagent is increasingly colored during the storage of the color reagent and the reagent blank increases with a lapse of time, it is necessary to prepare a fresh color reagent when in use. To the contrary, the color reagent according to the present invention underwent no color change even after 24 hours.

Table 2 shows comparison in measurement results between Example 1 and Reference Example 3.

TABLE 2

| Serum No. | Example 1 (IU/l) | Reference Example 3 (IU/l) |
|---|---|---|
| 1 | 1.5 | 1.7 |
| 2 | 7.8 | 7.2 |
| 3 | 2.3 | 2.3 |
| 4 | 1.1 | 1.4 |
| 5 | 4.2 | 3.9 |
| 6 | 1.6 | 1.6 |
| 7 | 5.1 | 4.8 |
| 8 | 12.7 | 13.0 |
| 9 | 0.9 | 1.1 |
| 10 | 1.2 | 1.0 |
| average | 3.84 | 3.80 |

As shown in Table 2, the values in Example 1 are well correlated with Reference Example 3, and no significant differences therebetween are observed ($\gamma = 0.997$).

EXAMPLE 2

Quantitative analysis of free cholesterol in serum

To 0.05M of phosphate buffer solution (pH 7.0) were dissolved BSdiproPM, uricase, cholesterol oxidase, peroxidase, Triton X-100, and Emal NC, Triton and Emal NC being dissolved to be at concentrations of 0.05 mM, 300 U/l, 100 U/l, 3000 U/l, 0.15% and 0.05% respectively to prepare a color reagent.

3 ml of the above color reagent was added to 10 μl of sampled serum, which was incubated at 37° C. for 10 min. Then, absorbance at a wavelength of 620 nm was measured with reference to a reagent blank as control.

Figure 2:
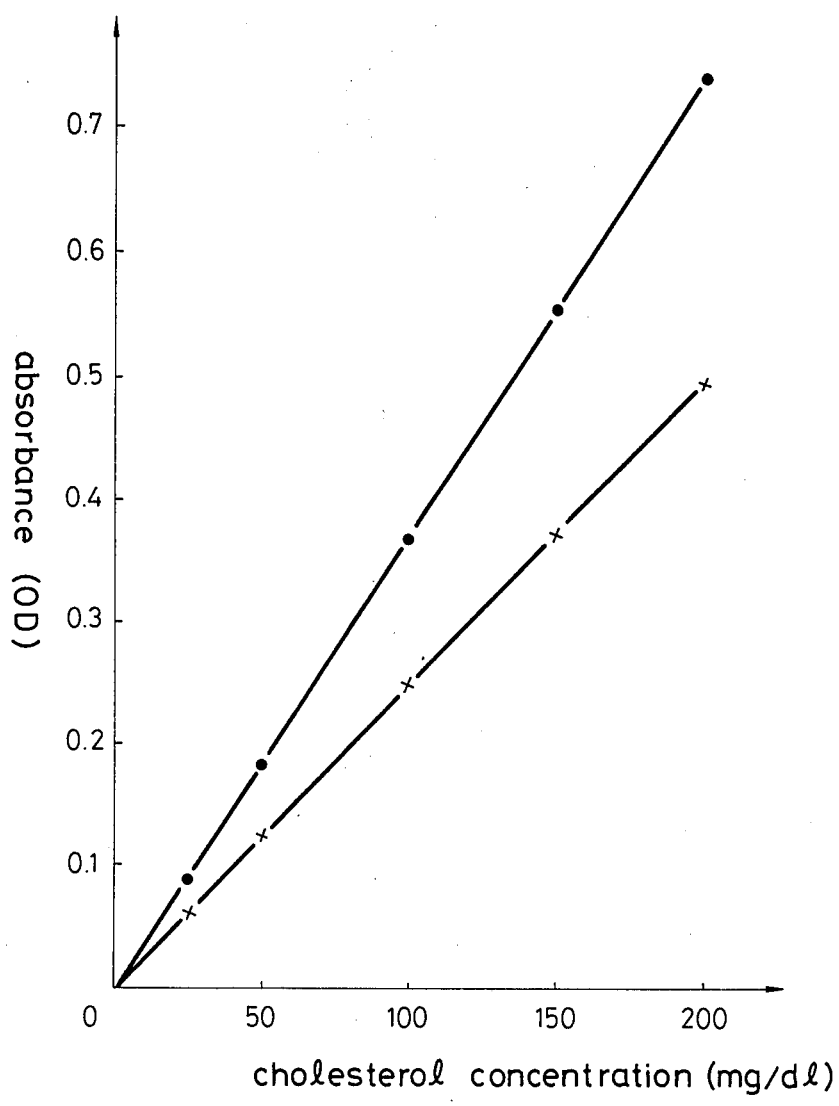
FIG. 2 shows calibration curves obtained in Example 2 and Reference Example 4 respectively (.—. being the calibration curve in Example 2 and x—x being the one in Reference Example 4) in which absorbances (OD) are plotted on the ordinate with respect to the respective cholesterol concentrations (mg/dl) on the abscissa, and the plotted points are connected.

Separately, cholesterol standard solutions were prepared to be at concentrations of 25, 50, 100, 150 and 200 mg/dl respectively, and aborbances were measured in the same manner as in the serum to obtain a calibration curve therefrom. FIG. 2 is shows a calibration curve.

The concentration of the cholesterol in the serum was determined from the calibration curve.

REFERENCE EXAMPLE 4

Quantitative analysis of free cholesterol in serum

To 0.05M phosphate buffer liquid (pH=7.0) were dissolved 4-aminoantipyrine, phenol, cholesterol oxidase, peroxidase, and Triton X-100 to be concentrations of 0.01%, 0.1%, 100 U/l, 3,000 U/l, and 0.1% respectively to prepare a color reagent.

3 ml of the above color reagent was added to 50 μl of sampled serum, which was incubated at 37° C. for 10 min. Then, absorbance was measured at a wavelength of 505 nm with reference to a reagent blank as control.

Separately, color was developed by using the cholesterol standard solutions (prepared in Example 2) in the same manner as above, and absorbances were measured to obtain a calibration curve therefrom. FIG. 2 shows the thus obtained calibration curve.

Table 3 shows comparison in measurement results between Example 2 and Reference Example 4.

TABLE 3

| | Measured value of cholesterol | | | |
|---|---|---|---|---|
| Serum No. | Example 2 mg/dl | Reference Example 4 mg/dl | No *1 uricase | Concentration *2 of uric acid |
| 1 | 41.8 | 43.1 | 20.7 | 4.1 |
| 2 | 34.0 | 34.7 | 5.4 | 8.5 |
| 3 | 40.8 | 43.1 | 17.0 | 4.8 |
| 4 | 29.3 | 30.6 | 6.2 | 5.7 |
| 5 | 62.3 | 62.1 | 35.2 | 6.3 |
| 6 | 64.6 | 63.3 | 40.6 | 4.3 |
| 7 | 27.8 | 28.6 | 1.7 | 9.3 |
| 8 | 54.1 | 50.4 | 22.9 | 5.2 |
| Average | 44.34 | 44.49 | | |

Note:
*1 "No uricase" means a case where measurement was carried out according to Example 2 with respect to a color reagent prepared from the components of the color reagent of Example 2 with uricase being excluded.
*2 "Concentration of uric acid" means the concentration of the uric acid measured by using Uric Acid B-Test wako (manufactured by Wako Pure Chemical Industries, Ltd.)

The significant difference in the measurement values between Example 2 and Reference Example 4 was examined using t-test method. The significance level was 5%, and no difference therebetween was observed. In the case of "no uricase", the measured values were largely lowered due to the uric acid in the serum, and negative influence due to the uric acid is obvious.

EXAMPLE 3

Quantitative anlysis of hydrogen peroxide

In 0.05M phosphate buffer solution (ph=7.0) were dissolved BSdiproPM, peroxidase and Triton X-100 to be at concentrations of 0.05 mM, 3,000 U/l and 0.05% respectively to prepare a color reagent.

3 ml of the above color reagent was added to 20 μl of a sample containing 1-60 ppm of $H_2O_2$, which was incubated at 37° C. for 10 min. Then, absorbance at a wavelength of 620 nm was measured with reference to a reagent blank as control.

Figure 3:
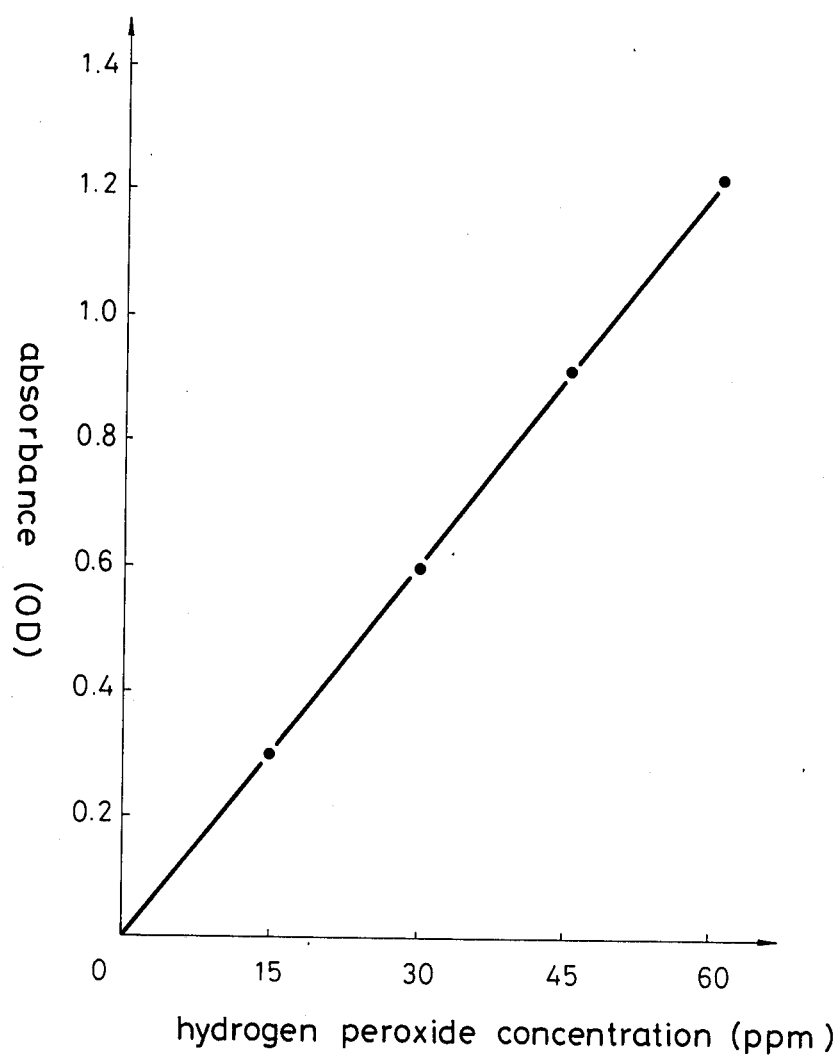
FIG. 3 shows a calibration curve obtained in Example 3 in which absorbances (OD) are plotted in an ordinate with respects to the respective hydrogen peroxide concentrations (ppm) in an abscissa, and the plotted points are connected.

Separately, by using hydrogen peroxide standard solutions prepared to be at concentrations of 15, 30, 45, and 60 ppm respectively were prepared, absorbances thereof were measured in the same manner as above to obtain a calibration curve therefrom. FIG. 3 shows the thus obtained calibration curve.

The concentration of the hydrogen peroxide in the sample was determined from the calibration curve.

EXAMPLE 4

Quantitative analysis of $H_2O_2$

To 0.05M of phosphate buffer solution (pH=7.0) were dissolved BSproPM, peroxidase, and Triton X-100 to be at concentration of 0.05 mM, 3,000 U/l and 0.05% respectively to prepare a color reagent.

Absorbance of the sample was measured in the same manner as in Example 3, and the concentration of the hydrogen peroxide in the sample was determined from a calibration curve obtained by using the separately prepared hydrogen peroxide standard solution (used in Example 3).

Figure 4:
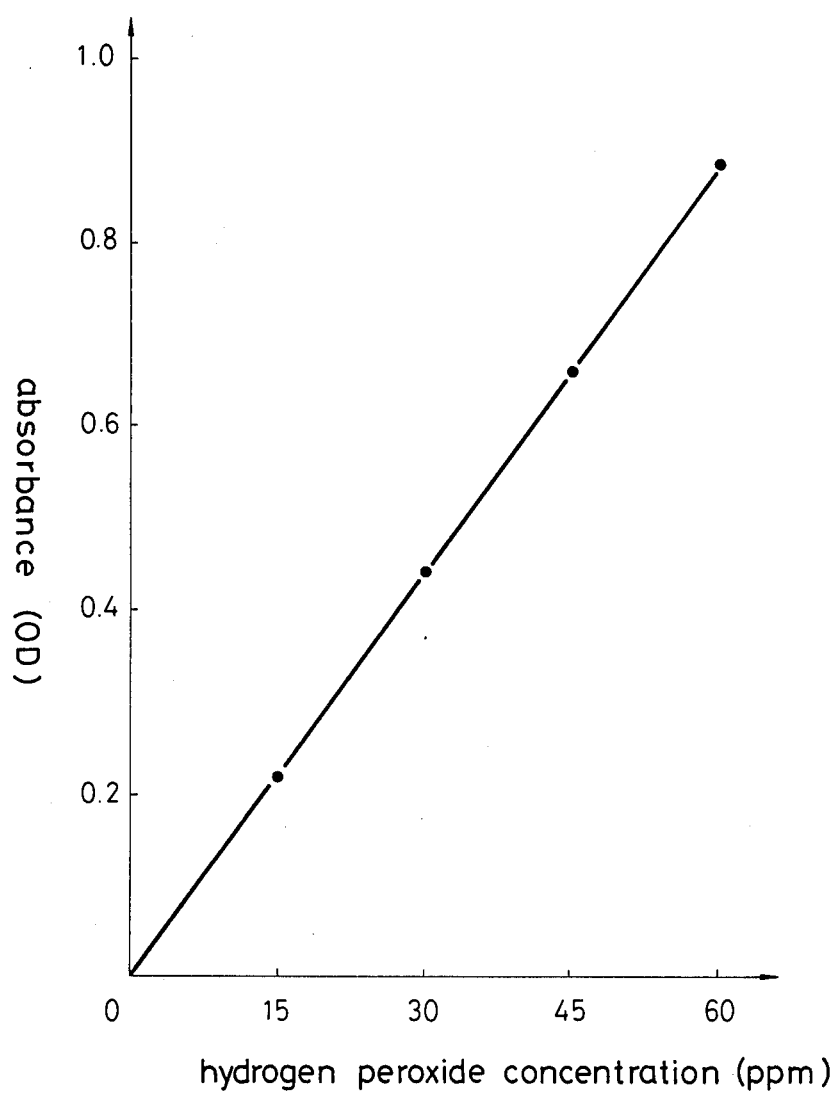
FIG. 4 shows a calibration curve obtained in Example 4 in which absorbances (OD) are plotted on the ordinate with respect to the respective hydrogen peroxide concentrations (ppm) on the abscissa, and the plotted points are connected.

FIG. 4 shows the calibration curve thus obtained.

EXAMPLE 5

Quantitative analysis of $H_2O_2$ in the presence of a coloring-interference inhibitor (1) Preparation of reagents:

(i) Color reagent:

A color reagent was prepared such that 0.05 mmol/l of BSdiproPM, 3,000 U/l of POD, and 2% of a surface active agent or 0.2% of metal chelate were contained in 0.05M of phosphate buffer solution (pH 7.0).

(ii) Albumin solution:

Into 5 g of human albumin (Albumin manufactured by Sigma Co., Ltd. Human Fraction V 96–99%) sample was added water to be 100 ml in a total volume.

(iii) Uric acid standard solution:

150 mg/l aqueous solution of uric acid was prepared according to the ordinary method.

(iv) $H_2O_2$ standard solutions:

Aqueous solutions containing 30 ppm and 60 ppm respectively were prepared as $H_2O_2$ standard solutions I and II.

(2) Measuring steps

As a sample, 50 μl of each of water, the albumin solution and the uric acid standard solution was sampled, and 3 ml of the color reagent was added to and mixed with the sample. Thereafter, 20 μl of the $H_2O_2$ standard solution I or II was added thereto, which was incubated at 37° C. for 10 minutes. Then, absorbance at a wavelength of 620 nm was measured with reference to a reagent blank as control.

Results are shown in Table 4.

TABLE 4

| Coloring-interference inhibitor | Water | | Albumin solution | | Uric acid standard solution | |
|---|---|---|---|---|---|---|
| | $H_2O_2$ standard solution | | | | | |
| | I | II | I | II | I | II |
| No addition | 0.684 | 1.372 | 0.624 | 1.248 | 0.094 | 0.142 |
| 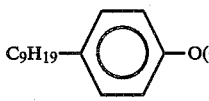 (anionic surface active agent) | 0.688 | 1.368 | 0.686 | 1.370 | 0.020 | 0.198 |
| Fe(III)-EDTA | 0.673 | 1.356 | 0.670 | 1.344 | 0.212 | 0.352 |
| Mn(II)-EDTA | 0.686 | 1.376 | 0.680 | 1.371 | 0.116 | 0.123 |
| Ni(II)-EDTA | 0.688 | 1.379 | 0.682 | 1.366 | 0.095 | 0.119 |

As apparent from Table 4, the coloring interferences of albumin can be avoided by using the anionic surface active agent or the metal chelate according to the present invention. However, the interference of uric acid can not be avoided by these additives.

EXAMPLE 6

Quantitative analysis of $H_2O_2$ in the presence of no coloring-interference inhibitor (1) Preparation of reagents (i) Color reagent:
Same as in Example 5 (no coloring-interference inhibitor contained)

(ii) Uric acid standard solutions:
Aqueous solutions of uric acid at concentrations of 0, 25, 50, 75 and 100 mg/l respectively were prepared according to the ordinary method.

(iii) $H_2O_2$ standard solutions:
Aqueous solutions containing 15, 30, 45 and 60 ppm of $H_2O_2$ respectively were prepared.

(2) Measuring steps

Absorbances were measured by using the uric acid standard solutions as sample according to the measuring steps in Example 5.

Figure 5:
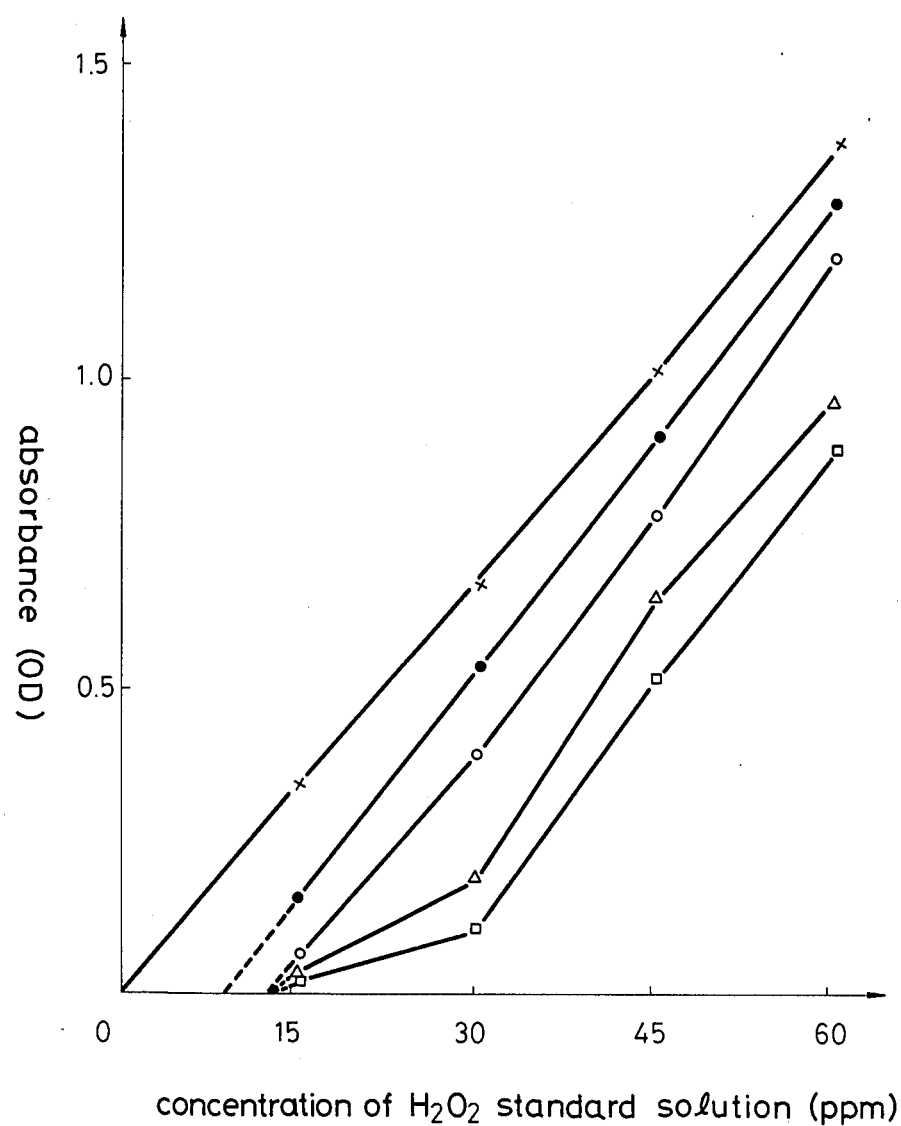
FIG. 5 illustrates results in Table 5 regarding Example 6, in which absorbances (OD) are plotted on the ordinate with respect to the respective concentration (ppm) $H_2O_2$ standard solutions on the abscissa, and the plotted points are connected together (—x—x—, —.—.—, —O—O—, —△—△—, and —□—□— show the calibration curves in the concentrations of the uric acid standard solutions, 0 mg/l (water), 25 mg/l, 50 mg/l, 75 mg/l and 100 mg/l respectively)

Results are shown in Table 5 and in FIG. 5.

TABLE 5

| Concentration of uric acid standard solution (mg/l) | $H_2O_2$ standard solution (ppm) | | | |
|---|---|---|---|---|
| | 15 | 30 | 45 | 60 |
| 0 | 0.343 | 0.675 | 1.025 | 1.374 |
| 25 | 0.159 | 0.537 | 0.917 | 1.281 |
| 50 | 0.062 | 0.393 | 0.789 | 1.197 |
| 75 | 0.033 | 0.193 | 0.651 | 0.972 |
| 100 | 0.025 | 0.105 | 0.520 | 0.892 |

As seen from Table 5 and FIG. 5, negative errors are produced by the presence of uric acid, and the calibration curve is curved and does not pass through the origin. The negative error becomes larger with the increase in the concentration of uric acid, but is in no proportion thereto.

EXAMPLE 7

Quantitative analysis of $H_2O_2$ in the presence of coloring-interference inhibitor (1) Preparation of reagents (i) Color reagent:
Same as in Example 5 (no coloring-interference inhibitor contained)

(ii) Uric acid standard solutions:
Same as in the above Reference Examples (iii) $H_2O_2$ standard solutions:
Same as in Example 6

(2) Measuring steps

To the color reagent was added uricase to be at the concentration of 200 U/l, and absorbances were measured by using the resulting solution as in the case of Example 6.

Results are shown in Table 6.

TABLE 6

| Concentration of uric acid (mg/l) | $H_2O_2$ standard solution (ppm) | | | |
|---|---|---|---|---|
| | 15 | 30 | 45 | 60 |
| 0 | 0.343 | 0.675 | 1.025 | 1.374 |
| 25 | 0.343 | 0.680 | 1.031 | 1.372 |
| 50 | 0.341 | 0.683 | 1.022 | 1.364 |
| 75 | 0.345 | 0.693 | 1.037 | 1.377 |
| 100 | 0.342 | 0.681 | 1.024 | 1.371 |

As seen from Table 6, the influences of uric acid are completely removed by using uricase, but no influence upon the measured value of $H_2O_2$ are produced thereby.

EXAMPLE 8

Measurement of activity of serum monoamine oxidase (1) Preparation of reagents (i) Substrate color reagent:

Allylamine, uricase, BSdiproPM, Emal NC (Kao Soap Co., Ltd., trademark), and POD were dissolved in 20 mM phosphate buffer solution (pH 7.0) to be at the concentrations of 15 m mol/l, 200 U/l, 0.03 m mol/l and 5% respectively.

(ii) Reaction terminator:

8.9 m mol/l aqueous solution of sodium diethyldithiocarbamate was prepared.

(iii) Monoamine oxidase solutions: 5 IU/l, 10 IU/l and 20 IU/l aqueous solutions were prepared by using bovine monoamine oxidase manufactured by Sigma Co., Ltd.

(2) Measuring steps

50 μl of serum was sampled, and 3 ml of the substrate color reagent was added thereto. After incubation at 37° C. for 30 minutes, 50 μl of the reaction terminator was added to and mixed the solution. Then, absorbances at a wavelength of 620 nm were measured with reference to a reagent blank as control.

The absorbances were measured by using the monoamine oxidase solution as in the case of the serum, and a calibration curve was drawn.

Figure 6:
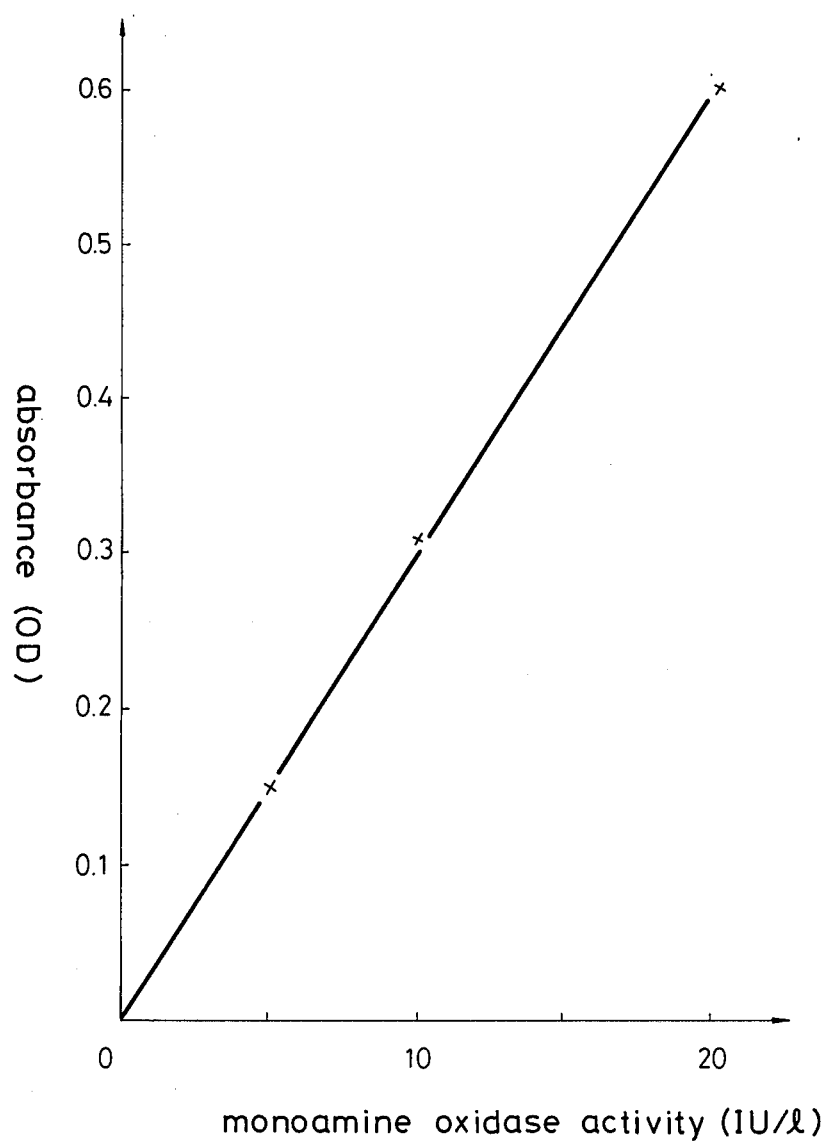
FIG. 6 shows a calibration curve obtained in Example 8 in which absorbances (OD) are plotted on the an ordinate with respect to the respective monoamine oxidase activities (IU/l) on the abscissa, and the plotted points are connected together.

FIG. 6 shows the calibration curve thus obtained.

The monoamine oxidase activity was determined from the calibration curve.

EXAMPLE 9

Quantitative analysis of an extremely small amount of hemoglobin in serum in the presence of a coloring-interference inhibitor (1) Preparation of reagents (i) Reagent solution I:

2 g of leucomalachite green was dissolved into 100 ml of a mixed solvent of acetic acid and water at the volume ratio of 3:1.

(ii) Reagent solution II:

30 g of glycine and 200 g of urea were dissolved into about 900 ml of water, and the solution was adjusted at pH 4.5 with hydrochloric acid, which was diluted with water to be 1,000 ml in a total volume after the addition of 30 g of Emal NC.

(iii) Reagent solution III:

Water was added to 1 ml of 30% $H_2O_2$ to be 100 ml in a total volume.

(iv) Uricase solution:

Uricase was dissolved into 0.05M phosphate buffer solution (pH 7.0) to give a concentration of 200 U/l.

(v) Serum:

Serum samples containing hemoglobin at the concentrations of 0.34, 0.68, 1.0, 1.5 and 2.0 mg/l respectively were prepared by adding hemoglobin to a pool serum (containing 50 mg/l of uric acid) containing no hemoglobin.

(2) Measuring steps

To 0.1 ml of serum sampled were added 1 ml of the uricase solution and 11 ml of the reagent solution, which was incubated at 37° C. for 5 minutes. Then, 1 ml of the reagent solution II and 0.2 ml of the reagent solution III were added thereto, which was further incubated at 37° C. for 60 minutes. Then, absorbances at 620 nm were measured with reference to a reagent blank as control.

Figure 7:
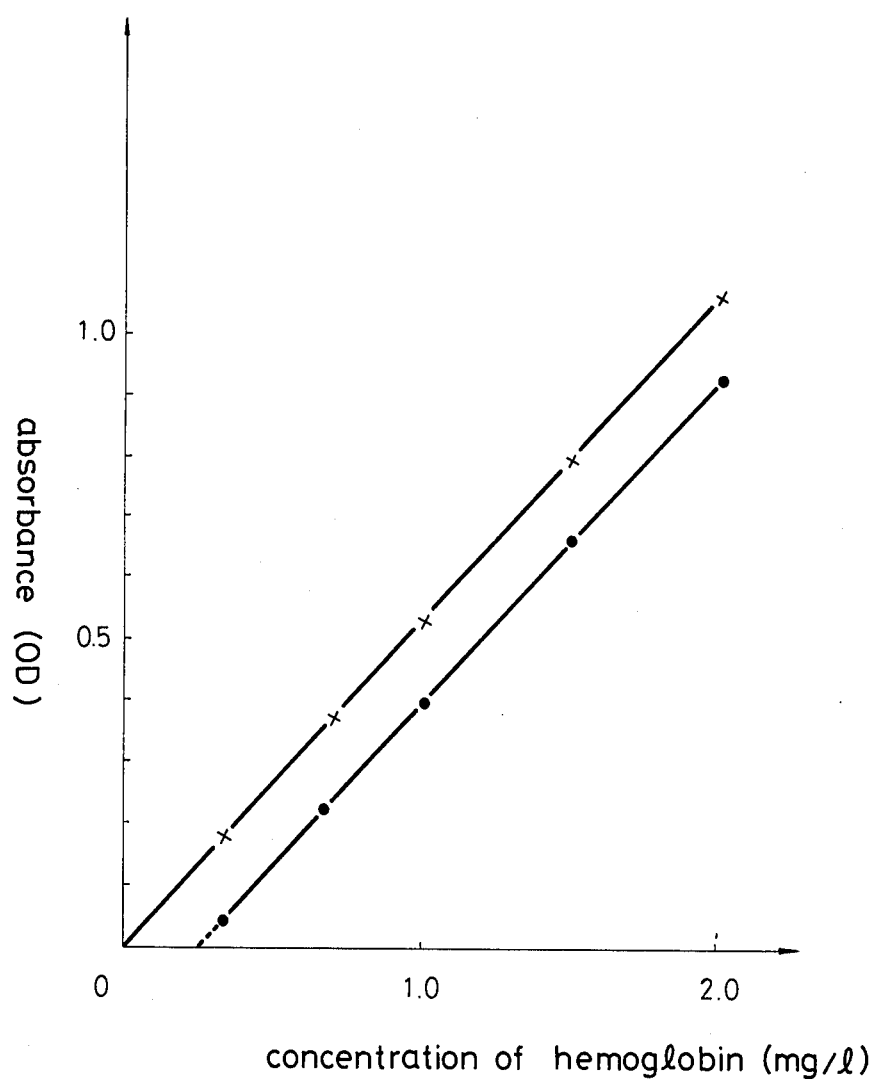
FIG. 7 shows calibration curves obtained in Examples 9 and 10 in which absorbances (OD) are plotted on the ordinate with respect to the respective concentrations (ppm) of hemoglobin (mg/l) on the abscissa, and the plotted points are connected together (—x—x—, and —.—.— shows the calibration curves in Examples 9 and 10 respectively)

FIG. 7 shows a calibration curve.

EXAMPLE 10

Quantitative analysis of an extremely small amount of hemoglobin in serum in the presence of a coloring-interference inhibitor (1) Preparation of reagents (i) Reagent solution I:

Same as in Example 9

(ii) Reagent solution II:

Same as the reagent solution II in Example 9 except that no Emal NC was contained.

(iii) Reagent solution III:

Same as in Example 9

(iv) Serum:

Same as in Example 9

(2) Measuring steps

To 0.1 ml of serum sampled were added 1 ml of 0.05M phosphate buffer solution (pH 7.0), 1 ml of the reagent solution I, 1 ml of the reagent solution II and 0.2 ml of the reagent solution III, which was subjected to the measurement of absorbances at 620 nm in the manner as in Example 9.

REFERENCE EXAMPLE 5

Quantitative analysis of $H_2O_2$ in the presence of sodium azide (1) Preparation of reagents (i) Color reagent:

A color reagent was prepared by dissolving into 0.05M phosphate buffer solution (pH 7.0), BSdiproPM, peroxidase, and sodium azide to be at concentrations of 0.05 m mol/l, 3,000 U/l and 0.2% respectively.

(ii) $H_2O_2$ standard solutions:

$H_2O_2$ aqueous solutions at concentrations of 15 mg/l, 30 mg/l, 45 mg/l, 60 mg/l and 75 mg/l respectively were prepared.

(iii) Measuring steps:

To 20 μl of each of the $H_2O_2$ standard solution sampled was added 3 ml of the color reagent, which was incubated at 37° C. for 10 minutes. Then, absorbances at 620 nm were measured with reference to a reagent blank as control.

Figure 8:
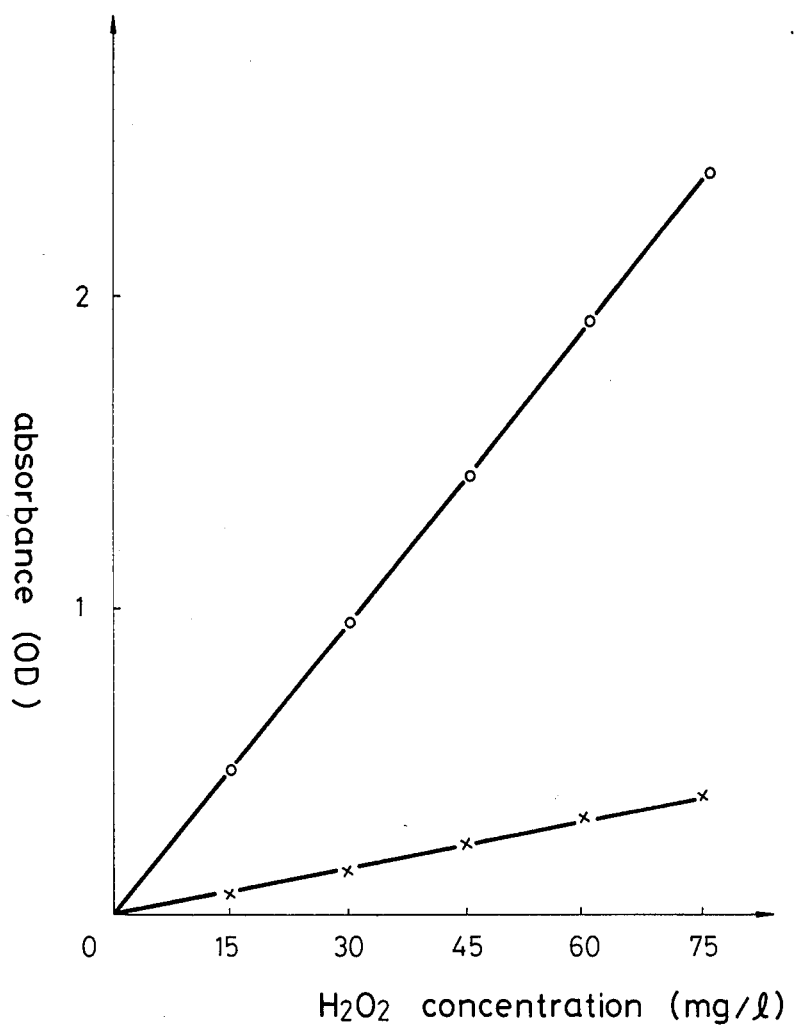
FIG. 8 shows calibration curves obtained in Reference Examples 5 and 6 in which absorbances (OD) are plotted on the ordinate with respect to the respective hydrogen peroxide concentrations (mg/l) on the abscissa, and the plotted points are connected together (—x—x— and — — — show the calibration curves in Reference Examples 5 and 6 respectively)

FIG. 8 shows a calibration curve, which is a straight line passing through the origin. When the concentration of $H_2O_2$ is 15 mg/l, the absorbance is 16.5% of the corresponding value in Reference Example 6 in which no sodium azide was used.

REFERENCE EXAMPLE 6

Quantitative analysis of $H_2O_2$ in the presence of no sodium azide (1) Preparation of reagents (i) Color reagent:

A color reagent of the same composition as that in Example 10 except that no sodium azide was contained was prepared.

(ii) $H_2O_2$ standard solutions:

Same as in Reference Example 5

(2) Measuring steps

Absorbances were measured in the same manner as in Reference Example 5.

FIG. 8 shows a calibration curve.

EXAMPLE 11

Quantitative analysis of whole cholesterol in the presence of sodium azide (1) Preparation of reagents (i) Color reagent:

A color reagent was prepared by dissolving into 0.1M trishydrochloric acid buffer solution (pH 7.0), BSdiproPM, uricase, cholesterol esterase, cholesterol oxidase, peroxidase, sodium azide and Triton X-100 to be at concentrations of 0.05 m mol/l, 300 U/l, 1,000 U/l, cholesterol oxidase 150 U/l, 3,000 U/l, 0.2%, and 0.15% respectively.

(ii) Cholesterol standard solutions:

Isopropanol solutions of cholesterol at concentrations of 100 mg/dl, 200 mg/dl, 300 mg/dl, 400 mg/dl and 500 mg/dl respectively were prepared.

(2) Measuring steps 3 ml of the above coloring test solution was added to 20 μl of each of the cholesterol standard solutions sampled, which was incubated at 37° C. for 10 minutes. Then, absorbances at 620 nm were measured with reference to a reagent blank as control, and a calibration curve was drawn.

Figure 9:
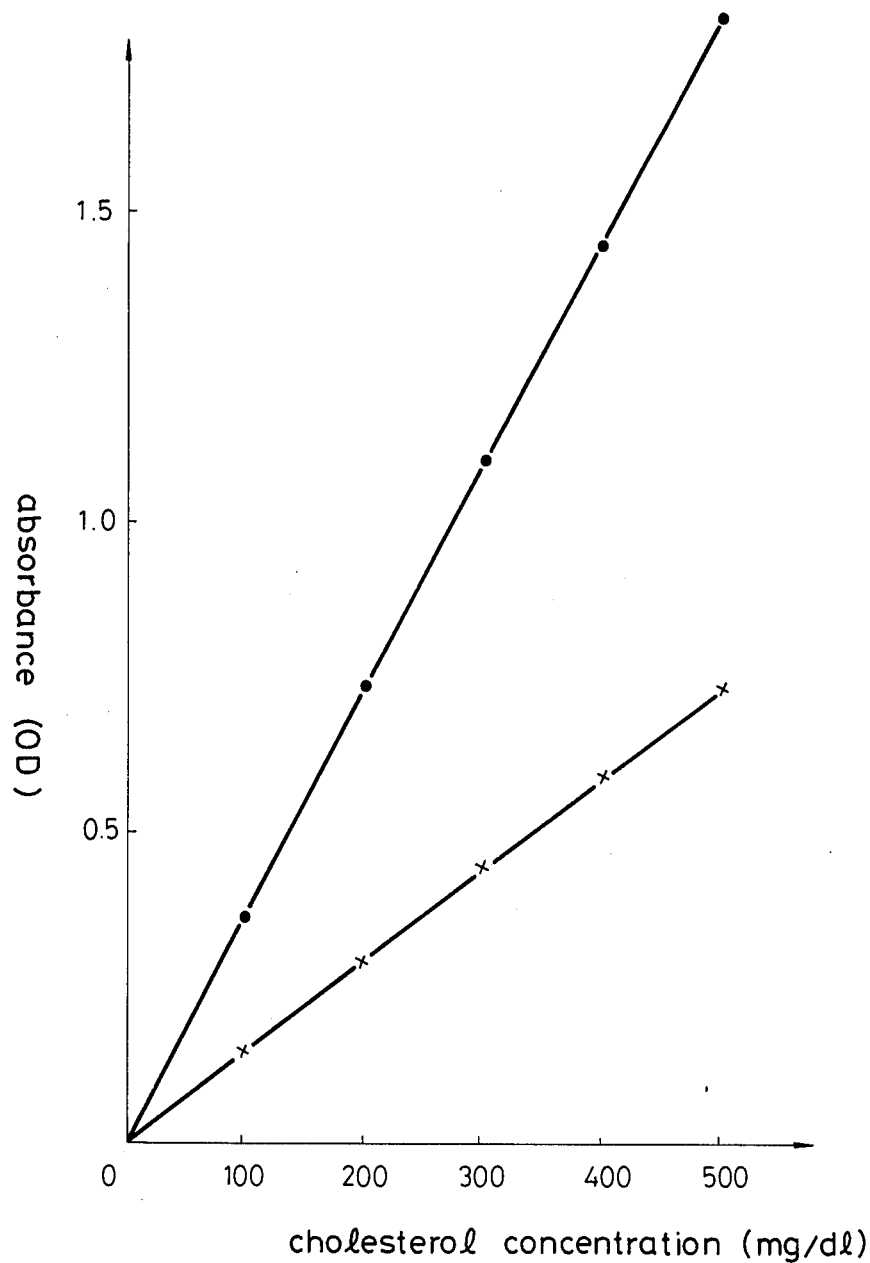
FIG. 9 shows calibration curves obtained in Reference Examples 11 and 7 in which absorbances (OD) are plotted on the ordinate with respect to the respective cholesterol concentrations (mg/dl) on the abscissa, and the plotted points are connected together (—x—x—, and —O—O— show the calibration curves in Reference Examples 11 and 7 respectively)

FIG. 9 shows the calibration curve thus obtained, which is a stright line passing through the origin. In the calibration curve, the absorbance is 0.290 at the cholesterol concentration of 200 mg/dl, and this measurements is suitable for the measurement by using the ordinary photometer.

REFERENCE EXAMPLE 7

Quantitative analysis of whole cholesterol in the presence of no sodium azide (1) Preparation of reagents (i) Coloring test solution A coloring test solution of the same composition of that in Example 11 except that no sodium azide was added was prepared.

(ii) Cholesterol standard solution:

Same as in Example 11

(2) Measuring steps

Absorbances were measured similarly to in Example 11. A calibration curve is shown in FIG. 9. Although the calibration curve is a straight line passing through the original, the absorbance is a high value of 0.731 at the cholesterol concentration of 200 mg/dl, and accuracy is poor in the case of the ordinary photometer using a logarithm scale.

REFERENCE EXAMPLE 8

Quantitative analysis of $H_2O_2$ in the presence of $\beta$-CD (1) Preparation of reagents (i) Color reagent:
Into 0.1M tris-hydrochloric acid buffer solution pH 7.5 were dissolved $\beta$-CD and peroxidase to be at concentrations of 0.2% and 6,000 U/l respectively, to which BSPM was dissolved at the concentration of 0.1 mM.

(ii) $H_2O_2$ standard solutions:

$H_2O_2$ standard solutions at concentrations of 15 mg/l, 30 mg/l, 45 mg/l, 50 mg/l and 75 mg/l respectively were prepared.

(2) Measuring steps:

3 ml of the color reagent was added to 20 μl of each $H_2O_2$ standard solution, which was incubated at 37° C. for 10 minutes. Then, absorbances at 630 nm were measured with reference to a reagent blank as control.

Figure 10:
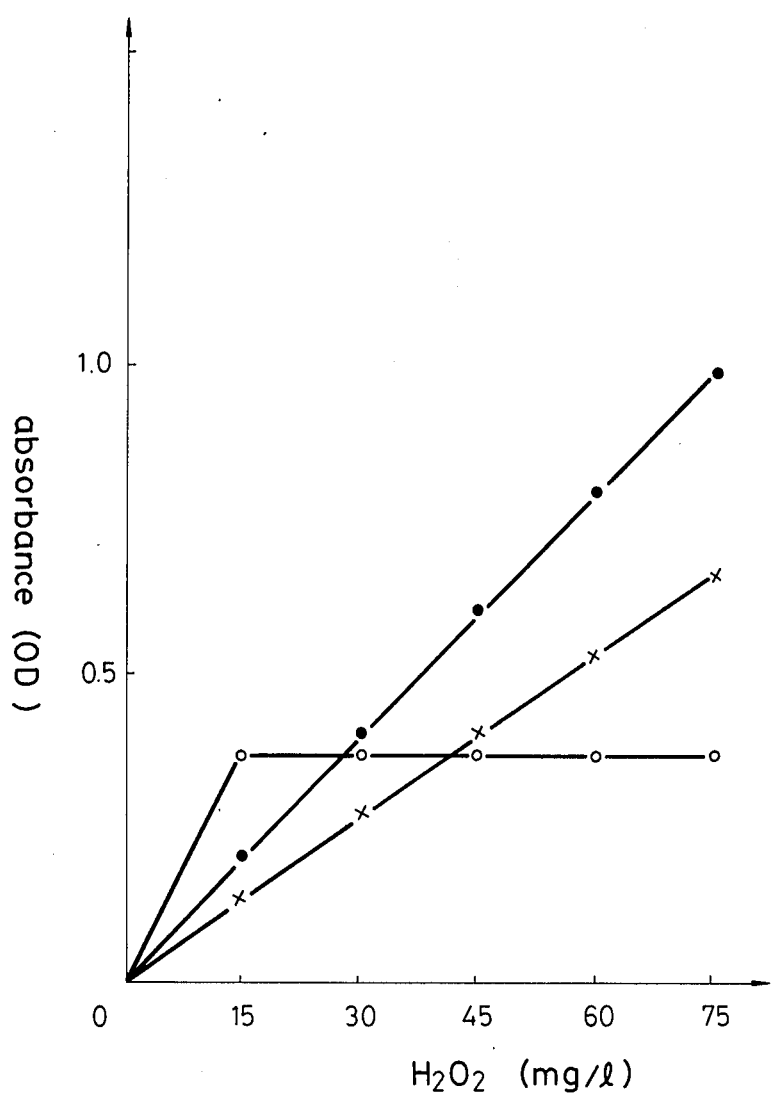
FIG. 10 shows calibration curves of $H_2O_2$ obtained in Reference Examples 8, 9 and 10 using BSPM as a coloring reagent in which —x—x—, —.—.— and —O—O— show the calibration curves in Reference Examples 8, 9 and 10 respectively.

FIG. 10 shows a calibration curve in which the absorbance is assigned to the ordinate, and the concentration of $H_2O_2$ is assigned to the abscissa. The calibration curve is a straight line passing through the origin. The absorbance at 15 ml/l of $H_2O_2$ is 37.4% of the corresponding value in Reference Example 10 using BSPM itself without being included.

REFERENCE EXAMPLE 9

Quantitative measurement of $H_2O_2$ in the presence of $\alpha$-CD (1) Preparation of Reagents (i) Color reagent:

A color reagent of the same composition as in Example 11 was prepared except that 0.2% of $\beta$-CD was substituted by 1% of $\alpha$-CD.

(ii) $H_2O_2$ standard solution:
Same as in Reference Example 8

(2) Measuring steps

Absorbances were measured in the same manner as in Example 11.

FIG. 10 shows a calibration curve, which is a straight line passing through the origin. The absorbance at 15 mg/l of $H_2O_2$ is 55.2% of the corresponding value in Reference Example 10.

REFERENCE EXAMPLE 10

Quantitative analysis of $H_2O_2$ in the presence of no CD (1) Preparation of reagents (i) Color reagent:
Into 0.1M tris-hydrochloric acid buffer solution (pH 7.5) were added and dissolved under stirring peroxidase and BSPM to be at concentrations of 6,000 U/l and 0.1 mM. At that time, since BSPM was not completely dissolved, an undissolved portion thereof was filtered off after 10 minutes stirring, and the filtrate was used as a color reagent.

(ii) $H_2O_2$ standard solutions:
Same as in Reference Example 8

(2) Measuring steps

Absorbances were measured in the same manner as in Reference Example 8. A calibration curve is shown in FIG. 10. Since the solubility of BSPM is low, the coloring reagent was insufficient, so that the calibration curve did not become a straight line.

REFERENCE EXAMPLE 11

Quantitative analysis of $H_2O_2$ in the presence of $\beta$-CD (1) Preparation of Reagents (i) Color reagent:

Into 0.1M tris-hydrochloric acid buffer solution (pH 7.5) were added and dissolved BSdiproPM, β-CD and peroxidase to be at concentrations of 0.1 mM, 0.2% and 6,000 U/l respectively.

(ii) $H_2O_2$ standard solutions:
Same as in Reference Example 8

(2) Measuring steps

Figure 11:
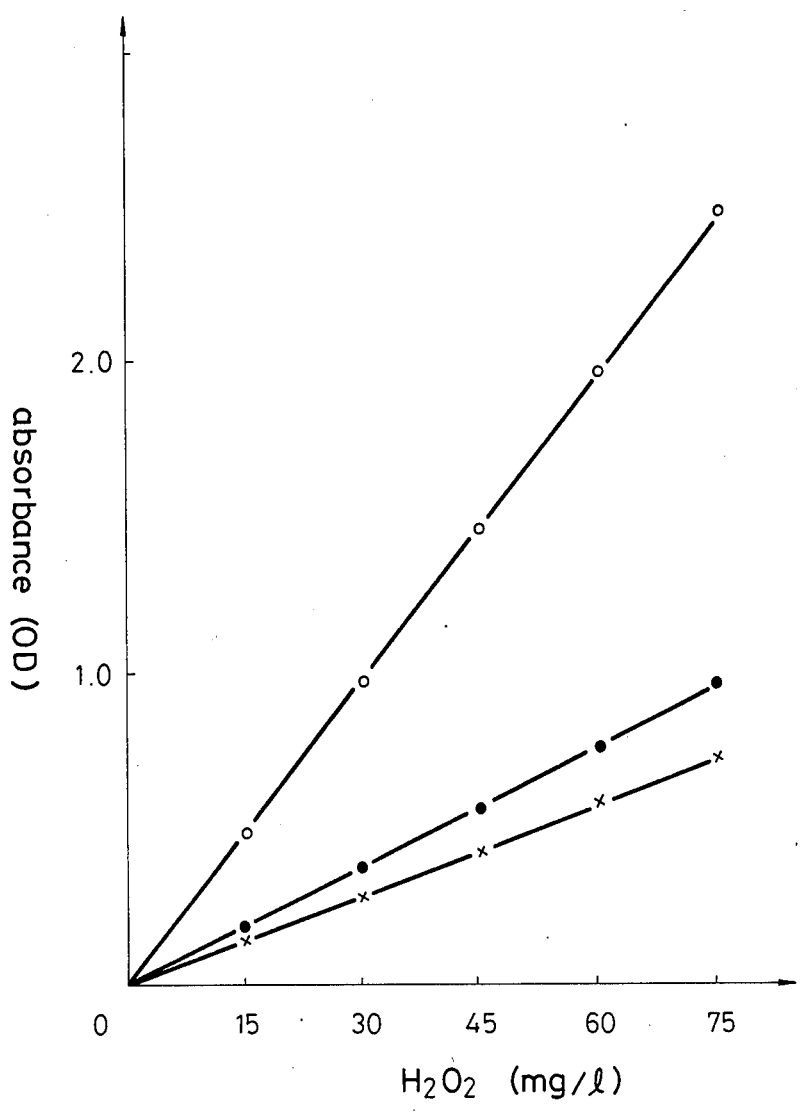
FIG. 11 shows calibration curves of $H_2O_2$ in Reference Examples 11, 12 and 13 using BSdiproPM as a coloring reagent in which —x—x—, —.—.— and —O—O— show the calibration curves in Reference Examples 11, 12 and 13 respectively.

Absorbances at a wavelength of 620 nm were measured in the same manner as in Reference Example 8. FIG. 11 shows a calibration curve, which is a straight line passing through the origin. The absorbance at 15 mg/l of $H_2O_2$ is 29.0% of the corresponding value in Reference Example 13 in which BSdiproPM was used as it was without being included.

REFERENCE EXAMPLE 12

Quantitative analysis of $H_2O_2$ in the presence of α-CD (1) Preparation of reagents (i) Color reagent:
A color reagent of the same composition as in Reference Example 11 was prepared except that 0.2% of β-CD was substituted by 1% of α-CD.
(ii) $H_2O_2$ standard solutions:
Same as in Reference Example 8

(2) Measuring steps

Absorbances were measured in the same manner as in Reference Example 11. FIG. 11 shows a calibration curve which is a straight line passing through the origin. The absorbance at 15 mg/l of $H_2O_2$ is 38.7% of the corresponding value in Reference Example 13.

REFERENCE EXAMPLE 13

Quantitative analysis of $H_2O_2$ in the presence of no CD (1) Preparation of reagents (i) Color reagent:
A color reagent of the same composition as in Reference Example 11 was prepared except that no β-CD was added.
(ii) $H_2O_2$ standard solutions:
Same as in Reference Example 8

(2) Measuring steps

Absorbances were measured in the same manner as in Reference Example 11. FIG. 11 shows a calibration curve which is a straight line passing through the origin.

Reference Example 14

Quantitative analysis of $H_2O_2$ in the presence of β-CD (1) Preparation of reagents (i) Color reagent:
Into 0.1M tris-hydrochloric acid buffer solution (pH 7.5) were added and dissolved BSproPM, β-CD and peroxidase to be at concentrations of 0.1 mM, 0.2% and 6,000 U/l respectively.
(ii) $H_2O_2$ standard solutions:
Same as in Reference Example 8

(2) Measuring steps

Figure 12:
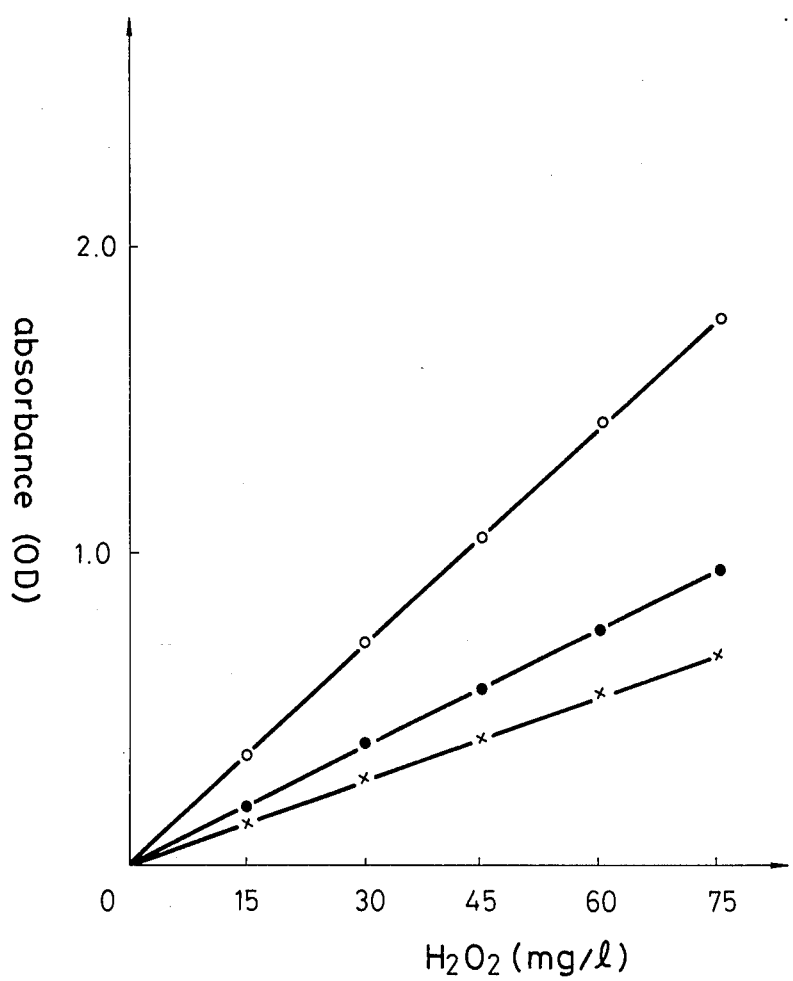
FIG. 12 shows calibration curves of $H_2O_2$ in Reference Examples 14, 15 and 16 using BSproPM as a coloring reagent in which —x—x—, —.—.— and —O—O— show the calibration curves in Reference Examples 14, 15 and 16 respectively.

Absorbances were measured in the same manner as in Reference Example 11. FIG. 12 shows a calibration curve, which is a straight line passing through the origin. The absorbance at 15 mg/l of $H_2O_2$ is 38.3% of the corresponding value in Reference Example 16 in which BSproPM was used as it was without being included.

REFERENCE EXAMPLE 15

Quantitative analysis of $H_2O_2$ in the presence of α-CD (1) Preparation of reagents (i) Color reagent:
A color reagent of the same composition as in Reference Example 14 was prepared except that 0.2% of β-CD was substituted by 1% of α-CD.
(ii) $H_2O_2$ standard solutions:
Same as in Reference Example 8

(2) Measuring steps

Absorbances were measured in the same manner as in Reference Example 11. FIG. 12 shows a calibration curve, which is a straight line passing through the origin. The absorbance at 15 mg/l of $H_2O_2$ is 53.7% of the corresponding value in Reference Example 16.

REFERENCE EXAMPLE 16

Quantitative analysis of $H_2O_2$ in the presence of no CD (1) Preparation of reagents (i) Color reagent:
A color reagent of the same composition as in Reference Example 14 was prepared except that no β-CD was added.
(ii) $H_2O_2$ standard solutions:
Same as in Reference Example 8

(2) Measuring steps

Absorbances were measured in the same manner as in Reference Example 11. FIG. 12 shows a calibration curve, which is a straight line passing through the origin.

EXAMPLE 12

Quantitative analysis of total cholesterol in the presence of β-CD (1) Preparation of reagents (i) Color reagent:
Into 0.1M tris-hydrochloric acid buffer solution (pH 7.0) were added and dissolved BSdiproPM, uricase, cholesterol oxidase, peroxidase, β-CD and Triton X-100 to be at concentrations of 0.05 mM, 300 U/l, 150 U/l, 3,000 U/l, 0.2% and 0.15% respectively to obtain a color reagent.
(ii) Cholesterol standard solutions:
Isopropanol solutions of cholesterol at concentrations of 100 mg/dl, 200 mg/dl, 300 mg/dl, 400 mg/dl, and 500 mg/dl respectively were prepared.

(2) Measuring steps

Figure 13:
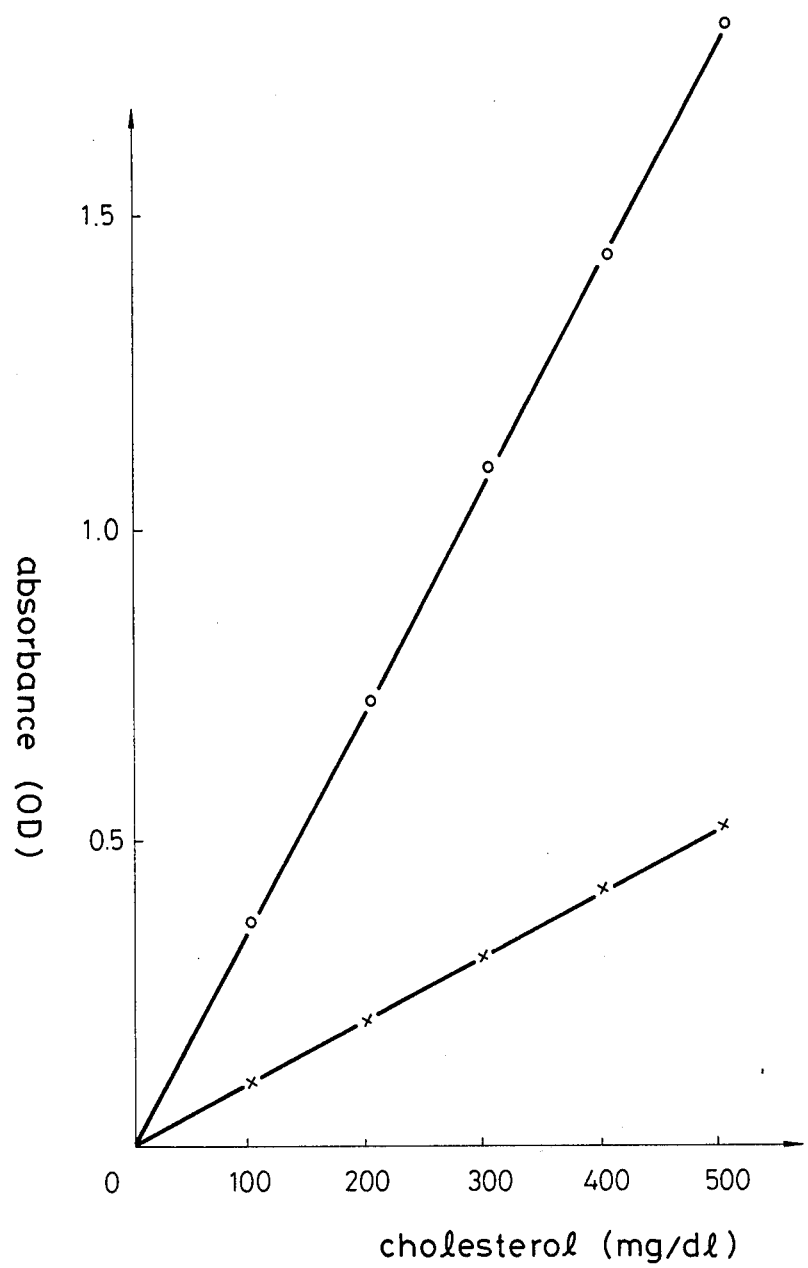
FIG. 13 shows calibration curves for quantitatively measuring the total cholesterol in Examples 12 and 13 by using BSdiproPM as
 a coloring reagent in which —x—x— and —O—O— show the calibration curves in Examples 12 and 13 respectively.

20 μl of each of the cholesterol standard solutions of the above respective concentrations was sampled and 3 ml of the coloring test solution was added thereto, which was incubated at 37° C. for 10 minutes. Then, absorbances at a wavelength of 620 nm were measured with reference to a blank reagent as control, and a calibration curve was drawn. FIG. 13 shows the calibration curve thus obtained, which is a straight line passing through the origin. The absorbance at the cholesterol concentration of 200 mg/dl is 0.210, which is the absorbance suitable for the measurement by using the ordinary photometer.

EXAMPLE 13

Quantitative analysis of total cholesterol in the presence of modified β-CD (1) Preparation of reagent (i) Color reagent:

A color reagent was prepared by adding and dissolving into 0.1M tris-hydrochloric acid buffer solution (pH 7.0), BSdiproPM, uricase, choresterol oxidase, peroxidase, heptakis(2,6-di-O-methyl)-β-cyclodextrin and Triton X-100 to be at a concentrations of 0.05 mM, 300 U/l, 150 U/l, 3,000 U/l, 0.3% and 0.15% respectively.

(ii) Cholesterol standard solutions:
Same as in Example 12

(2) Measuring steps

Figure 14:
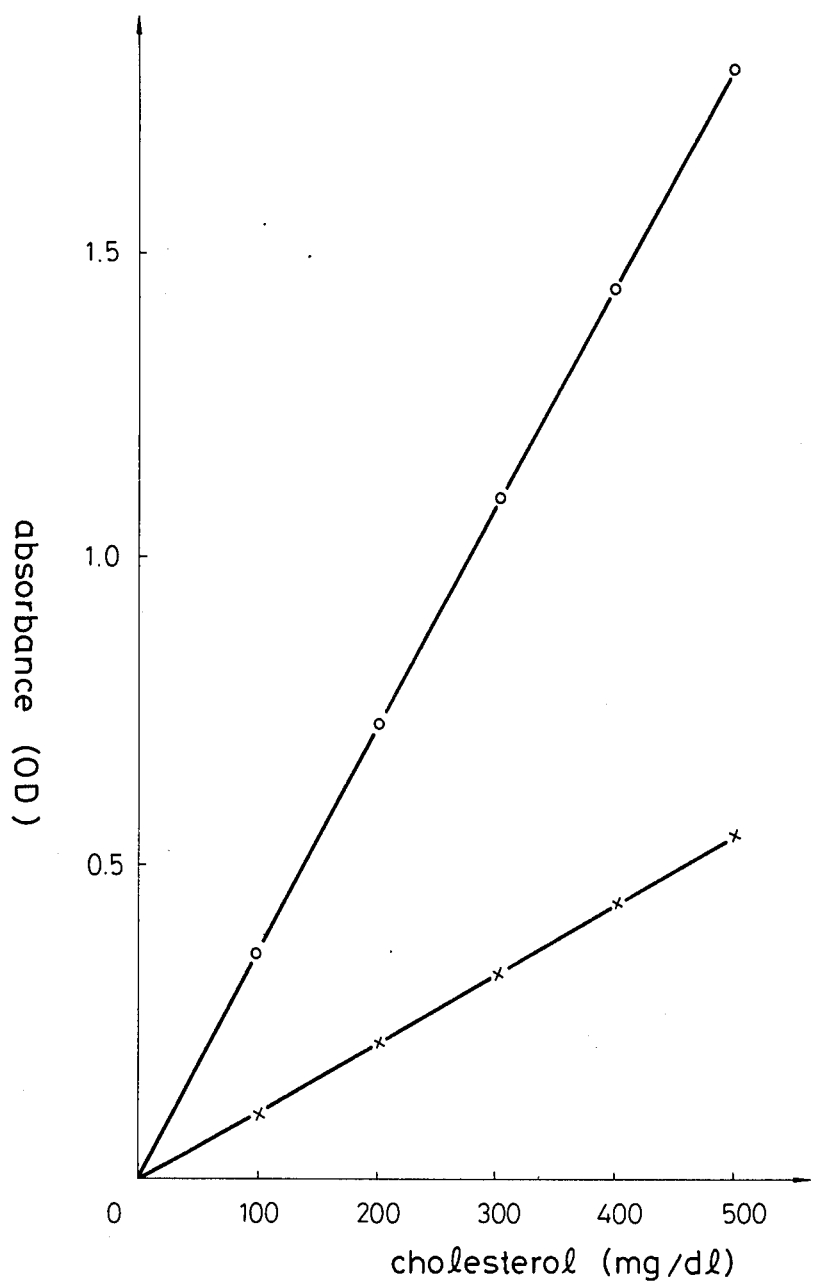
FIG. 14 shows calibration curves for quantitatively measuring the total cholesterol in Examples 13 and 14 by using BSdiproPM as a coloring reagent in which —x—x—and —O—O— show the calibration curves in Examples 13 and 14 respectively.

According to the measuring steps in Example 12, absorbances at a wavelength of 620 nm were measured, and a calibration curve was drawn. FIG. 14 shows the calibration curve thus obtained, which is a straight line passing through the origin. The absorbance at the cholesterol concentration of 200 mg/dl is 0.220, which is an absorbance suitable for the measurement by using the ordinary photometer.

EXAMPLE 14

Quantitative analysis of total cholesterol in the presence of no β-CD (1) Preparation of reagents (i) Color reagent:

A color reagent of the same composition as in Example 12 was prepared except that no β-CD was added.

(ii) Cholesterol standard solutions:
Same as in Example 12

(2) Measurement steps

Absorbances were measured in the same manner as in Example 12. A calibration curve is shown in FIG. 13 (FIG. 14). Although the calibration curve is a straight line passing through the origin, the absorbance at the cholesterol concentration of 200 mg/dl is a high value of 0.731. Thus, this method is poor in accuracy in the measurement by using a photometer using a logarithm scale.

EXAMPLE 15

Quantitative analysis of triglyceride in the presence of β-CD (1) Preparation of reagents (i) Color reagent:

Preparation was made of a solution of 0.05M tris-hydrochloric acid buffer solution (pH 7.5) containing 0.05 mM of BSdiproPM, 300 U/l of uricase, 5,000 U/l of lipoprotein lipase, 4,000 U/l of glycerokinase, 1,000 U/l of glycerol-3-phosphoric acid oxidase, 3,000 U/l of peroxidase, 0.2% of β-CD, 1,000 mg/l of ATP, 5 mM of magnesium chloride, 0.1% of Triton X-405 and 1.0% of Emal NC (Kao Soap Co., Ltd., trademark)

(ii) Glycerol standard solutions:

Preparation were made of an aqueous glycerol solutions at concentrations of 10.4 mg/dl, 20.8 mg/dl, 31.2 mg/dl, 41.6 mg/dl, 52.0 mg/dl and 62.4 mg/dl respectively (corresponding to the concentrations of 100 mg/dl, 200 mg/dl, 300 mg/dl, 400 mg/dl, 500 mg/dl, and 600 mg/dl as triolein respectively).

(2) Measuring steps 3 ml of the color reagent was added to 20 82 1 of sampled serum, which was incubated at 37° C. for 10 minutes. Then, absorbances at a wavelength of 620 nm were measured with reference to a reagent blank as control.

Figure 15:
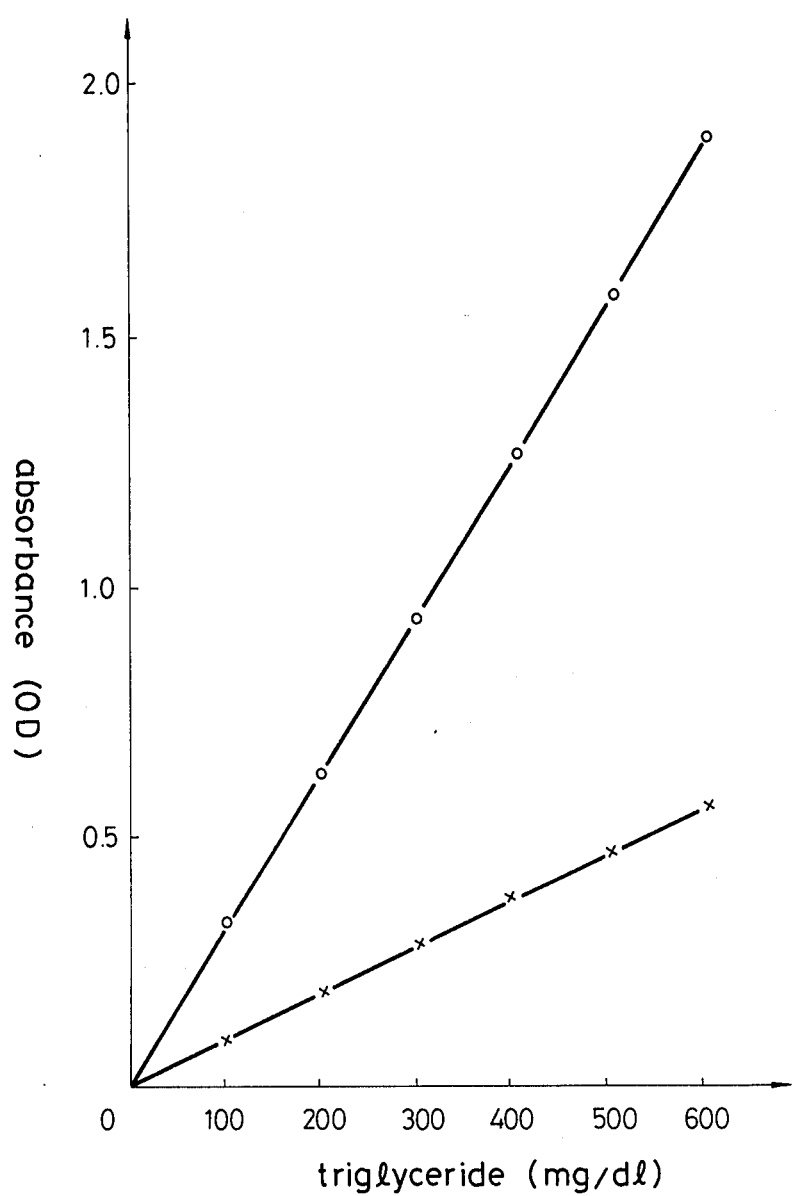
FIG. 15 shows calibration curves for quantitatively measuring triglyceride in Examples 14 and 15 by using BSdiproPM as a coloring reagent in which —x—x— and —O—O— show the calibration curves in Examples 14 and 15 respectively.

Meanwhile, 3 ml of the color reagent was added to 20 μl of each of the sampled glycerol standard solution of the above respective concentrations, which was subjected to the measurement of absorbances in the same manner as in the case of the serum to obtain a calibration curve. FIG. 15 shows the calibration curve thus obtained, which is a straight line passing through the origin. The absorbances at the triglyceride concentration of 200 mg/dl is 0.185, which is an absorbance suitable for the measurement by using the ordinary photometer.

EXAMPLE 16

Quantitative analysis of triglyceride in the presence of no β-CD (1) Preparation of reagents (i) Color reagent:

A color reagent of the same composition in Example 15 was prepared except that no β-CD was added.
(ii) Glycerol standard solutions:
Same as in Example 14

(2) Measuring steps

Similarly to Example 15, the glycerol standard solutions of the above respective concentrations were colored, and their absorbances were measured, from which a calibration curve was drawn. The calibration curve thus drawn is shown in FIG. 15. Although the calibration curve is a straight line passing through the origin, the absorbance at the triglyceride concentration of 300 mg/dl is a high value of 0.951. Therefore, the accuracy is poor in the measurement by using a photometer of a logarithm scale.

In the following Table is shown a comparison in the measured values of serum triglyceride between Example 15 and Example 16.

TABLE 7

| Comparison in the measured value of serum triglyceride | | | | | |
|---|---|---|---|---|---|
| Serum | Example 15 | Example 16 | Serum | Example 15 | Example 16 |
| 1 | 83 mg/dl | 78 mg/dl | 7 | 267 mg/dl | 265 mg/dl |
| 2 | 600 | 618 | 8 | 379 | 373 |
| 3 | 96 | 106 | 9 | 187 | 193 |
| 4 | 77 | 68 | 10 | 98 | 101 |
| 5 | 133 | 134 | | | |
| 6 | 115 | 119 | Average | 203.5 | 205.5 |

γ = 0.999

As shown in Table 7, the significant value between Examples 15 and 16 are γ=0.999, and they exhibit a good correlation.

What is claimed is:

1. A method of quantitatively measuring an oxidative substance, or a substance having peroxidase activity, in the presence of coloring-interfering substances comprising the steps of reacting the oxidative substance with a triphenyl methane type leuco coloring reagent represented by the general formula (I):

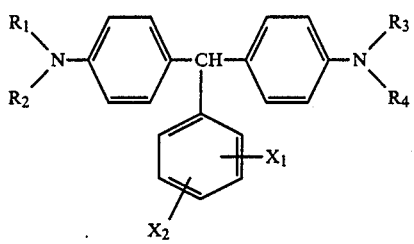

wherein $R_1$, $R_2$, $R_3$ and $R_4$ each independently represents a hydrogen atom or a lower alkyl group, and $X_1$ and $X_2$ each independently represents a hydrogen atom, $-SO_3M_1$, $-COOM_2$, $-O(CH_2)_mSO_3M_3$, $-O(CH_2)_nCOOM_4$ or $-N(R_5)(R_6)$ in which $M_1$, $M_2$, $M_3$ and $M_4$ each independently represents a hydrogen atom, an alkali metal ion or $NH_4+$, $R_5$ and $R_6$ each independently represents a hydrogen atom or a lower alkyl group, and m and n each independently represents 2, 3, or 4, in the presence of at least one of (i) uricase, (ii) an anionic surface active agent or (iii) a metal chelate compound; and quantitating colorimetrically the oxidation of the coloring reagent.

2. The method according to claim 1, wherein the oxidative substance is hydrogen peroxide generated by acting an oxidation enzyme upon a substrate or a substance produced in an enzyme reaction.

3. The method according to claim 2, wherein the coloring reagent is oxidized in the presence of peroxidase, and the coloring is colorimetrically measured, whereby $H_2O_2$ is quantitatively measured.

4. The method according to claim 2, wherein said substrate is a body fluid component selected from the group consisting of glucose, cholesterol, triglyceride, phospholipid, choline, creatine, creatinine, and bile acid.

5. The method according to claim 2, wherein said oxidation enzyme is monoamine oxidase.

6. The method according to claim 1, wherein said substance having peroxidase activity is quantitatively measured by quantitatively measuring its peroxidase activity.

7. The method according to claim 6, wherein the substance having peroxidase activity is hemoglobin or a heme compound other than hemoglobin.

8. The method according to claim 1, wherein the coloring-interfering substance is uric aid, the influences of said uric acid being avoided by the addition of uricase.

9. The method according to claim 1, wherein the coloring-interfering substance is protein, the influences of said protein being avoided by the addition of an anionic surface active agent.

10. The method according to claim 1, wherein the coloring-interfering substance is protein, the influences of said protein being avoided by the addition of metal chelate compound.

11. The method according to claim 1, wherein the coloring-interfering substances are uric acid and protein, the influences of said uric acid being avoided by the addition of uricase, the influences of said protein being avoided by the addition of an anionic surface active agent.

12. The method according to claim 4, wherein the coloring-interfering substances are uric cid and protein, the influences of said uric acid being avoided by the addition of uricase, the influences of said protein being avoided by the addition of an anionic surface active agent.

13. The method according to claim 7, wherein the coloring-interfering substances are uric acid and protein, the influences of said uric acid being avoided by the addition of uricase, the influences of said protein being avoided by the addition of an anionic surface active agent.

14. The method according to claim 1, wherein the coloring-interfering substances are uric acid and protein, the influences of said uric acid being avoided by the addition of uricase, the influences of said protein being avoided by the addition of a metal chelate compound.

15. The method according to claim 4, wherein the coloring-interfering substances are uric acid and protein, the influences of said uric acid being avoided by the addition of uricase, the influences of said protein being avoided by the addition of a metal chelate compound.

16. The method according to claim 7, wherein the colorig-interfering substances are uric acid and protein, the influences of said uric acid being avoided by the addition of uricase, the influences of said protein being avoided by the addition of a metal chelate compound.

17. The method according to claim 9, wherein the anionic surface active agent is represented by one of the general formulae (II) and (III):

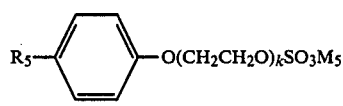

$$R_6O(CH_2CH_2O)_lSO_3M_6 \qquad (III)$$

in which $R_5$ is an alkyl group of 8-9 carbon atoms, $R_6$ represents an alkyl group of 8-18 carbon atoms, $M_5$ and $M_6$ each represent an alkali metal ion, an ammonium ion or a quaternary ammonium ion, and k and l each represent an integer of 1-6.

18. The method according to claim 10, wherein the metal chelate compound is a metal-EDTA (ethylenediamine tetraacetric acid) chelate.

19. A method of quantitatively measuring an oxidative substance, or a substance having peroxidase activity, in the presence of color-interfering substances comprising the steps of reacting the oxidative substance with a triphenyl methane type leuco coloring reagent represented by the general formula (I):

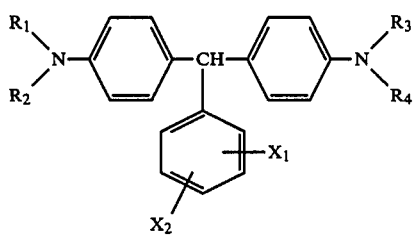

wherein R1, R2, R3 and R4 each independently represents a hydrogen atom or a lower alkyl group and $X_1$ and $X_2$ each independently represents a hydrogen atom, $-SO_3M_1$, $-COOM_2$, $-O(CH_2)_mSO_3M_3$, $-O(CH_2)_nCOOM_4$ or $-N(R_5)(R_6)$ n which $M_1$, $M_2$, $M_3$ and $M_4$ each independently represents a hydrogen atom, an alkali metal ion or $NH_4+$, $R_5$ and $R_6$ each independently represents a hydrogen atom or a lower alkyl group and m and n each independently represents 2, 3, or 4, in the presence of at least one of (i) uricase, (ii) an anionic surface active agent or (iii) a metal chelate compound capable of avoiding the influences of a coloring-interfering substance, and an azide capable of adjusting a coloring sensitivity; and quantitating colorimetrically the oxidation of the coloring reagent.

20. The method according to claim 19, wherein said azide is sodium azide.

21. The method according to claim 19, wherein the coloring reagent is oxidized in the presence of peroxidase, and coloring thereof is colorimetrically measured.

22. The method according to claim 21, wherein the oxidative substance is hydrogen peroxide, and said hydrogen peroxide is generated by an enzyme reaction.

23. The method according to claim 22, wherein the hydrogen peroxide is hydrogen peroxide which is generated by the enzyme reaction in the quantitative measurement of a minor component in a sample from a living organism.

24. The method according to claim 23, wherein the quantitative measurement of the minor component in the sample from the living organism is carried out by acting an oxidative enzyme upon a substrate or substance produced in an enzyme reaction to generate hydrogen peroxide, and by quantitatively measuring the hydrogen peroxide thus generated.

25. A method of quantitatively measuring an oxidative substance or a substance having peroxidase activity, in the presence of color-interfering substances comprising the steps of reacting the oxidative substance with a triphenyl methane type leuco coloring reagent represented by the general formula (I):

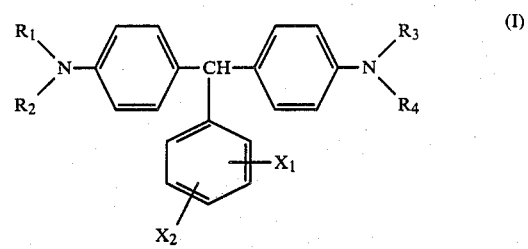

wherein $R_1$, $R_2$, $R_3$ and $R_4$ each independently represents a hydrogen atom or a lower alkyl group, and $X_1$ and $X_2$ each independently represents a hydrogen atom, $-SO_3M_1$, $-COOM_2$, $-O(CH_2)_mSO_3M_3$, $-O(CH_2)_nCOOM_4$ or $-N(R_5)(R_6)$ in which $M_1$, $M_2$, $M_3$ and $M_4$ each independently represents a hydrogen atom, an alkali metal ion or $NH_4+$, $R_5$ and $R_6$ each independently represents a hydrogen atom or a lower alkyl group and m and n each independently represents 2, 3, or 4, said triphenyl methane derivative being included with cyclodextrin or modified cyclodextrin, in the presence of at least one of (i) uricase, (ii) an anionic surface active agent or (iii) a metal chelate compound;

and quantitating colorimerically the oxidation of the coloring reagent.

26. The method according to claim 25, wherein the coloring reagent is oxidized in the presence of peroxidase, and coloring thereof is colorimetrically measured.

27. The method according to claim 25, wherein the oxidative substance is hydrogen peroxide, said hydrogen peroxide being generated by an enzyme reaction.

28. The method according to claim 27, wherein the hydrogen peroxide is generated by the enzyme reaction in a quantitative measurement of a minor component in a sample from a living organism.

29. The method according to claim 28, wherein the quantitative measurement of the minor component in the sample from the living organism is a quantitative measurement of one selected from a substrate and an enzyme activity in a sample from a living organism, which is carried out by acting an oxidation enzyme upon a substrate or substance produced by enzyme reaction to produce hydrogen peroxide, and quantitatively measuring hydrogen peroxide thus produced.

* * * * *